(12) United States Patent
Anderson et al.

(10) Patent No.: US 9,486,239 B2
(45) Date of Patent: Nov. 8, 2016

(54) SUBINTIMAL RE-ENTRY DEVICE

(71) Applicant: Boston Scientific Scimed, Inc., Maple Grove, MN (US)

(72) Inventors: James Anderson, Fridley, MN (US); Derek Sutermeister, Ham Lake, MN (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 335 days.

(21) Appl. No.: 13/900,717

(22) Filed: May 23, 2013

(65) Prior Publication Data

US 2013/0317528 A1 Nov. 28, 2013

Related U.S. Application Data

(60) Provisional application No. 61/651,273, filed on May 24, 2012.

(51) Int. Cl.
*A61B 17/22* (2006.01)
*A61B 17/34* (2006.01)
*A61B 17/3207* (2006.01)
*A61M 25/01* (2006.01)

(52) U.S. Cl.
CPC ....... *A61B 17/3417* (2013.01); *A61B 17/3207* (2013.01); *A61M 25/0194* (2013.01); *A61B 2017/22044* (2013.01); *A61B 2017/22095* (2013.01); *A61M 25/0136* (2013.01); *A61M 2025/0197* (2013.01)

(58) Field of Classification Search
CPC ............ A61M 2025/0197; A61M 2025/0095; A61M 25/0194; A61M 2025/018; A61M 25/0169; A61B 17/3417; A61B 2017/22095; A61B 10/02; A61B 10/0233; A61B 2017/00252; A61B 2017/22077
USPC ....... 606/159, 158, 139, 153, 167, 185, 213; 604/523; 623/1.23; 600/36, 585
See application file for complete search history.

(56) References Cited

U.S. PATENT DOCUMENTS 5,201,323 A * 4/1993 Vermeulen ............. A61B 10/02
600/569
5,830,222 A 11/1998 Makower
5,935,108 A 8/1999 Katoh et al.
5,938,671 A 8/1999 Katoh et al.

(Continued)

FOREIGN PATENT DOCUMENTS

CA 2887799 A1 11/2005
EP 1598015 A1 11/2005

(Continued)

*Primary Examiner* — Melanie Tyson
*Assistant Examiner* — Majid Jamialahmadi
(74) *Attorney, Agent, or Firm* — Seager, Tufte & Wickhem LLP

(57) ABSTRACT

A subintimal recanalization catheter, including an elongate shaft including a first tubular member and a penetration member slidably disposed in a lumen of the first tubular member. The penetration member includes a distal tip positioned proximal of a distal nose of the first tubular member. The distal nose of the first tubular member includes a ramp and a guide wire lumen extending through the distal nose of the first tubular member. Longitudinal movement of the penetration member relative to the first tubular member causes the penetration member to contact the ramp to direct the distal tip of the penetration member away from the first tubular member.

14 Claims, 18 Drawing Sheets

(56) References Cited

U.S. PATENT DOCUMENTS

| | | |
|---|---|---|
| 5,968,064 A | 10/1999 | Selmon et al. |
| 6,010,449 A | 1/2000 | Selmon et al. |
| 6,068,638 A | 5/2000 | Makower |
| 6,120,516 A | 9/2000 | Selmon et al. |
| 6,159,225 A | 12/2000 | Makower |
| 6,190,353 B1 | 2/2001 | Makower et al. |
| 6,217,527 B1 | 4/2001 | Selmon et al. |
| 6,217,549 B1 | 4/2001 | Selmon et al. |
| 6,221,049 B1 | 4/2001 | Selmon et al. |
| 6,231,546 B1 * | 5/2001 | Milo et al. ............... 604/164.13 |
| 6,231,587 B1 | 5/2001 | Makower |
| 6,235,000 B1 | 5/2001 | Milo et al. |
| 6,241,667 B1 | 6/2001 | Vetter et al. |
| 6,398,798 B2 | 6/2002 | Selmon et al. |
| 6,506,178 B1 | 1/2003 | Schubart et al. |
| 6,508,825 B1 | 1/2003 | Selmon et al. |
| 6,511,458 B2 | 1/2003 | Milo et al. |
| 6,514,217 B1 * | 2/2003 | Selmon et al. ............... 600/585 |
| 6,579,302 B2 | 6/2003 | Duerig et al. |
| 6,599,304 B1 | 7/2003 | Selmon et al. |
| 6,638,247 B1 | 10/2003 | Selmon et al. |
| 6,663,577 B2 | 12/2003 | Jen et al. |
| 6,719,725 B2 | 4/2004 | Milo et al. |
| 6,955,175 B2 | 10/2005 | Stevens et al. |
| 7,004,173 B2 | 2/2006 | Sparks et al. |
| 7,179,270 B2 | 2/2007 | Makower |
| 7,229,421 B2 | 6/2007 | Jen et al. |
| 7,357,794 B2 | 4/2008 | Makower et al. |
| 7,740,623 B2 | 6/2010 | Nayak et al. |
| 7,918,859 B2 | 4/2011 | Katoh et al. |
| 7,918,870 B2 | 4/2011 | Kugler et al. |
| 7,938,819 B2 | 5/2011 | Kugler et al. |
| 8,025,655 B2 | 9/2011 | Kugler et al. |
| 8,083,727 B2 | 12/2011 | Kugler et al. |
| 2001/0000041 A1 | 3/2001 | Selmon et al. |
| 2001/0012924 A1 | 8/2001 | Milo et al. |
| 2002/0103459 A1 | 8/2002 | Sparks et al. |
| 2002/0128677 A1 | 9/2002 | Duerig et al. |
| 2003/0109809 A1 | 6/2003 | Jen et al. |
| 2003/0120195 A1 | 6/2003 | Milo et al. |
| 2003/0139763 A1 | 7/2003 | Duerig et al. |
| 2004/0167554 A1 | 8/2004 | Simpson et al. |
| 2004/0230219 A1 | 11/2004 | Roucher, Jr. |
| 2005/0171478 A1 | 8/2005 | Selmon et al. |
| 2006/0094930 A1 | 5/2006 | Sparks et al. |
| 2006/0184011 A1 | 8/2006 | Macaulay et al. |
| 2006/0276749 A1 * | 12/2006 | Selmon et al. ........... 604/164.01 |
| 2007/0093779 A1 | 4/2007 | Kugler et al. |
| 2007/0093780 A1 | 4/2007 | Kugler et al. |
| 2007/0093781 A1 | 4/2007 | Kugler et al. |
| 2007/0093782 A1 | 4/2007 | Kugler et al. |
| 2007/0208368 A1 | 9/2007 | Katoh et al. |
| 2007/0265596 A1 | 11/2007 | Jen et al. |
| 2008/0033423 A1 | 2/2008 | Peacock |
| 2008/0125748 A1 | 5/2008 | Patel |
| 2008/0154172 A1 | 6/2008 | Mauch |
| 2008/0200896 A1 | 8/2008 | Shmulewitz et al. |
| 2008/0228171 A1 | 9/2008 | Kugler et al. |
| 2008/0243065 A1 | 10/2008 | Rottenberg et al. |
| 2008/0243067 A1 | 10/2008 | Rottenberg et al. |
| 2008/0249397 A1 | 10/2008 | Kapadia |
| 2009/0005754 A1 * | 1/2009 | Soetermans ...... A61M 25/0169 604/500 |
| 2009/0005755 A1 | 1/2009 | Keith et al. |
| 2009/0088685 A1 | 4/2009 | Kugler et al. |
| 2009/0093791 A1 | 4/2009 | Heuser |
| 2009/0124899 A1 | 5/2009 | Jacobs et al. |
| 2009/0209910 A1 | 8/2009 | Kugler et al. |
| 2009/0254107 A1 | 10/2009 | Katoh et al. |
| 2009/0264826 A1 | 10/2009 | Thompson |
| 2009/0292296 A1 | 11/2009 | Pansky et al. |
| 2009/0299171 A1 | 12/2009 | Duffy et al. |
| 2009/0299402 A1 | 12/2009 | Orihashi et al. |
| 2010/0063534 A1 | 3/2010 | Kugler et al. |
| 2010/0069945 A1 | 3/2010 | Olson et al. |
| 2010/0125244 A1 | 5/2010 | McAndrew |
| 2010/0317973 A1 | 12/2010 | Nita |
| 2011/0112564 A1 | 5/2011 | Wolf |
| 2011/0144677 A1 | 6/2011 | Ward et al. |
| 2011/0166591 A1 | 7/2011 | Katoh et al. |
| 2013/0006167 A1 | 1/2013 | Alvarez et al. |
| 2013/0006173 A1 | 1/2013 | Alvarez et al. |
| 2013/0072957 A1 | 3/2013 | Anderson |
| 2014/0371718 A1 | 12/2014 | Alvarez et al. |

FOREIGN PATENT DOCUMENTS

| | | |
|---|---|---|
| JP | 2002525163 A | 8/2002 |
| JP | 2005334645 A | 12/2005 |
| WO | 0018323 A2 | 4/2000 |
| WO | 2013036419 | 3/2013 |

* cited by examiner

SUBINTIMAL RE-ENTRY DEVICE

CROSS-REFERENCE TO RELATED APPLICATION

The present application claims benefit of U.S. Patent Application No. 61/651,273, filed May 24, 2012, the complete disclosure of which is incorporated hereby by reference.

TECHNICAL FIELD

This disclosure relates to devices and methods for recanalization of an occluded blood vessel. More particularly, the disclosure is directed to devices and methods for re-entry into the true lumen from the subintimal space of the blood vessel.

BACKGROUND

Chronic Total Occlusion (CTO) is an arterial vessel blockage that obstructs blood flow through a vessel, and it can occur in both coronary and peripheral arteries. In some instances, it may be difficult or impossible to penetrate the CTO with a medical device in an antegrade direction to recanalize the vessel. Accordingly, techniques have been developed for creating a subintimal pathway (a path between the intimal and adventitial tissue layers of the vessel wall) around the occlusion and then re-entering the true lumen of the vessel distal of the occlusion. In some instances, re-entering the true lumen from the subintimal space and/or recanalization pathway may be difficult. Accordingly, it is desirable to provide alternative recanalization devices and/or methods having improved re-entry mechanisms for recanalization of a blood vessel in which a CTO is present.

SUMMARY

The disclosure is directed to several alternative designs and methods of using medical device structures and assemblies, and uses thereof.

Accordingly, one illustrated embodiment is a catheter for recanalizing a blood vessel having an occlusion therein. The catheter includes an elongate shaft having a proximal end, a distal end, and a guide wire lumen extending therethrough to a distal guide wire port. The elongate shaft includes a proximal portion having a tubular shape and a distal portion having a flattened shape, the flattened shape including first and second wings extending in opposite directions configured to facilitate orientation of the distal portion within a subintimal space of a vessel. A deflection wire extends from the proximal end to the distal end of the elongate shaft, wherein actuation of the deflection wire causes the distal portion of the elongate shaft to deflect into a curved configuration to orient the distal guide wire port toward a true lumen of the vessel.

Another illustrative embodiment for re-entry into the true lumen from the subintimal space is a catheter including an elongate shaft including a first tubular member and a penetration member slidably disposed in a lumen of the first tubular member. The penetration member includes a distal tip positioned proximal of a distal nose of the first tubular member. The distal nose of the first tubular member includes a ramp and a guide wire lumen extending through the distal nose of the first tubular member. The longitudinal movement of the penetration member relative to the first tubular member causes the penetration member to contact the ramp to direct the distal tip of the penetration member away from the first tubular member.

Yet another illustrative embodiment is a method for recanalizing a blood vessel having an occlusion therein. The method includes advancing a guide wire through a lumen of a blood vessel to a location proximal of a proximal end of an occlusion. A distal end of the guide wire is directed out of the lumen of the blood vessel and between a first tissue layer and a second tissue layer of a wall of the vessel to a location distal of a distal end of the occlusion. A recanalization catheter is advanced along the guide wire with the guide wire passing through a guide wire lumen of the recanalization catheter. The recanalization catheter includes a first tubular member and a penetration member slidably disposed in a lumen of the first tubular member. The penetration member includes a distal tip positioned proximal of a distal nose of the first tubular member, and the distal nose of the first tubular member includes a ramp and the guide wire lumen extending through the distal nose of the first tubular member. Furthermore, the distal nose is positioned between the first tissue layer and the second tissue layer at a location distal of the distal end of the occlusion. The penetration member is actuated relative to the first tubular member to cause the penetration member to contact the ramp and direct the distal tip of the penetration member away from the first tubular member, and re-enter the lumen of the blood vessel distal of the distal end of the occlusion.

The above summary of some example embodiments is not intended to describe each disclosed embodiment or every implementation of the present disclosure.

BRIEF DESCRIPTION OF THE DRAWINGS

The invention may be more completely understood in consideration of the following detailed description of various embodiments in connection with the accompanying drawings, in which:

FIG. 1A depicts the distal portion, and FIGS. 1B and 1C exhibit two alternative embodiments of the proximal portion of the catheter;

Figure 1A:
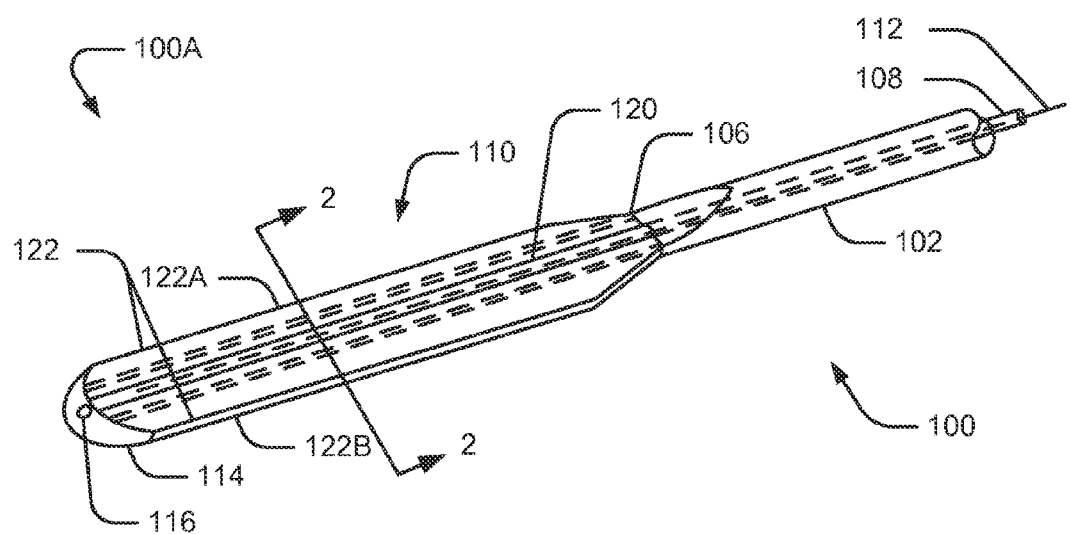
FIGS. 1A-1C illustrate an exemplary subintimal recanalization catheter, where

While the invention of the present disclosure is amenable to various modifications and alternative forms, specifics thereof have been shown by way of example in the drawings and will be described in detail. It should be understood, however, that the intention is not to limit aspects of the invention to the particular embodiments described. On the contrary, the intention is to cover all modifications, equivalents, and alternatives falling within the spirit and scope of the invention.

DETAILED DESCRIPTION

For the following defined terms, these definitions shall be applied, unless a different definition is provided in the claims or elsewhere in this specification. All numeric values are herein assumed to be modified by the term "about," whether or not explicitly indicated. The term "about" generally refers to a range of numbers that one of skill in the art would consider equivalent to the recited value (i.e., having the same function or result). In many instances, the term "about" may be indicative as including numbers that are rounded to the nearest significant figure.

The recitation of numerical ranges by endpoints includes all numbers within that range (e.g., 1 to 5 includes 1, 1.5, 2, 2.75, 3, 3.80, 4, and 5).

Although some suitable dimensions ranges and/or values pertaining to various components, features, and/or specifications are disclosed, one of skill in the art, incited by the present disclosure, would understand desired dimensions, ranges and/or values may deviate from those expressly disclosed.

As used in this specification and the appended claims, the singular forms "a," "an," and "the" include plural referents unless the content clearly dictates otherwise. As used in this specification and the appended claims, the term "or" is generally employed in its sense including "and/or" unless the content clearly dictates otherwise.

The following detailed description should be read with reference to the drawings in which similar elements in different drawings are numbered the same. The detailed description and the drawings, which are not necessarily to scale, depict illustrative embodiments and are not intended to limit the scope of the invention. The illustrative embodiments depicted are intended only as exemplary. Selected features of any illustrative embodiment may be incorporated into an additional embodiment unless clearly stated to the contrary.

While the devices and methods described herein are discussed relative to recanalization of arterial vessels blocked by a CTO, it is contemplated that the devices and methods may be used in other applications, where recanalization of a blood vessel is desired.

The present disclosure provides methods and systems to re-enter the true lumen of a blood vessel during recanalization of the blood vessel. To this end, the methods and systems may employ a catheter having a catheter shaft, a distal nose, and a penetration member, including a guide wire, and a guide wire lumen disposed within the catheter.

Exemplary Embodiments

Figure 1B:
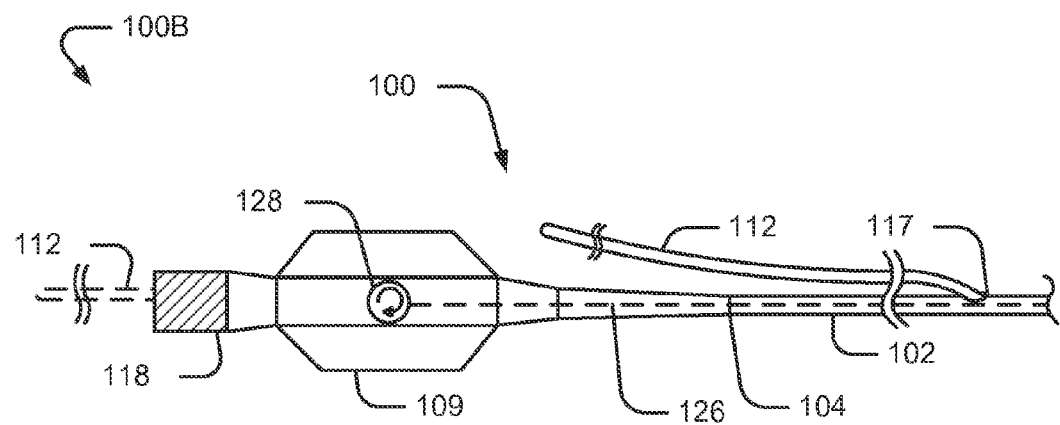
Figure 1C:
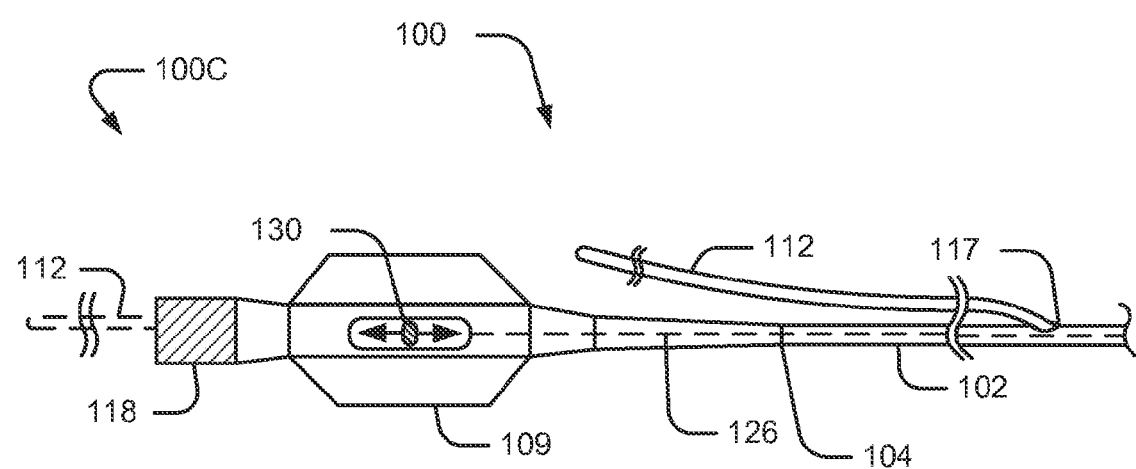

An exemplary subintimal recanalization catheter 100 is illustrated in FIGS. 1A-1C. The catheter 100 includes a distal portion 100A shown in FIG. 1A, and a proximal portion 100B shown in FIG. 1B. Further, an alternative embodiment of a proximal portion 100C is shown in FIG. 1C, respectively.

As illustrated in FIGS. 1A-1C, the catheter 100 may include a first tubular member, an outer catheter shaft 102 extending between a proximal end 104 (shown in FIGS. 1B-C) and a distal end 106. In addition, in some instances a second member, penetration member 108, may be slidably disposed within the catheter shaft 102 between the proximal end 104 and the distal end 106. In some embodiments, typically, a guide wire 112 may act as the penetration member 108. In other instances, a separate penetration member 108 may be used. A hub assembly 109 having one or more ports may connect to the proximal end 104, and a distal nose 110 may engage with the catheter shaft 102 at the distal end 106. The guide wire 112 may be slidably disposed within the penetration member 108 and the distal nose 110. In some instances, the guide wire 112 may be the penetration member 108. A distal tip 114 is disposed at the distal end of the distal nose 110, and the distal tip 114 may include a guide wire port 116 to extend the guide wire 112 or the penetration member 108 distally beyond catheter 100.

The catheter 100 may be configured to be advanced over the guide wire 112 for delivery to a remote location in the vasculature of a patient. In some embodiments, the catheter 100 may be configured as a Single Operator Exchange (SOE) (Monorail or Rapid-Exchange) catheter having a rapid exchange port 117 near the distal end 106 for inserting the guide wire 112 into a guide wire lumen 120. Alternatively, in some other embodiments, the catheter 100 may be configured as an Over The Wire (OTW) catheter having a port 118 configured at hub assembly 109 for inserting the guide wire 112 into the guide wire lumen 120. It may be noted that in instances where the catheter 100 is an SOE, the proximal end 104 may not include the port 118. Where the catheter 100 is an OTW, however, the rapid exchange port 117 may be omitted.

As shown in FIGS. 1A-1C, the catheter shaft 102 may be an elongate sheath or a tubular member adapted to move forward into a blood vessel lumen. The catheter shaft 102 may be configured with a substantially circular cross section extending between the proximal and distal ends 104, 106. Other suitable cross-sectional shapes of the catheter shaft 102 may be elliptical, oval, polygonal, or irregular. In addition, the catheter shaft 102 may be flexible along its entire length or adapted for flexure along portions of its length. Flexibility may allow the catheter shaft 102 to navigate through turns in body lumens, while rigidity provides the necessary force to urge the catheter shaft 102 forward. The cross-sectional dimensions of the catheter shaft 102 may vary according to the desired application, but they are generally smaller than the typical thickness of the blood vessel wall in locations where the catheter 100 may be used, such as in a coronary artery. The length of the catheter shaft 102 may vary according to the location of the vessel lumen where subintimal recanalization is to be conducted. In addition, the distal end 106 of the catheter shaft 102 may have a tapering structure similar to a wedge or a cone. Alternatively, the distal end 106 may not have a tapering structure. The hub assembly 109 at the proximal end 104 may include components such as one or more ports to insert various medical devices into the lumen of the catheter shaft 102. Furthermore, the hub assembly 109 may include a handle (not shown) for the operator to hold the catheter 100, and one or more actuation means (not shown) to control the guide wire 112 and/or the distal nose 110.

Catheter shaft 102 may be made of any suitable biocompatible material such as a polymeric or metallic material. The catheter shaft 102 may also be coated using a suitable low friction material, such as TEFLON®, polyetheretherketone (PEEK), polyimide, nylon, polyethylene, or other lubricious polymer coatings, to reduce surface friction with the surrounding tissues.

In instances in which the penetration member 108 is used in addition to the guide wire 112, the penetration member 108 may be an elongate sheath slidably disposed within the guidewire lumen 120 of the catheter shaft 102, where the guide wire 112 may be also slidably disposed coaxially therewith. In other instances, only one of the penetration member 108 and the guide wire 112 may be present in the guidewire lumen 120 at the same time, thus requiring removal of one of the guide wire 112 or the penetration member 108 prior to advancing the other of the guide wire 112 or the penetration member 108 through the guidewire lumen 120. The penetration member 108 may extend from the rapid exchange port 117 to the distal end 106 in instances in which the catheter 100 is an SOE catheter, or the penetration member 108 may extend from port 118 to the distal end 106 in instances in which the catheter 100 is an OTW catheter. The penetration member 108 may have a substantially circular cross-section. Alternatively, the cross-sectional shape of the penetration member 108 may be any shape in which the guide wire 112 may easily maneuver, for instance, oval, polygonal, or tapering or any other shape capable of achieving the intended purpose in the intended environment. The penetration member 108 may be flexible or adapted for flexure along portions of its length. The flexibility of the penetration member 108 may or may not depend upon the flexibility of the catheter shaft 102. The cross-sectional dimensions of the penetration member 108 may be greater than the cross-sectional dimensions of the guide wire 112 and less than the cross-sectional dimensions of the catheter shaft 102. The distal end of the penetration member 108 may or may not engage with the distal nose 110 at the distal end 106. In some embodiments, such as catheter 100 illustrated in FIGS. 1A-1C, the distal end of the penetration member 108 may connect to the distal nose 110. Moreover, the lumen of the penetration member 108 may be co-axial with the lumen of the distal nose 110 such that the guide wire 112 may pass from the penetration member 108 to the distal nose 110 without obstruction.

In some embodiments, the penetration member 108 may be formed of a metallic material, including a stainless steel or a nickel-titanium alloy such as nitinol. Alternatively, a polymeric material such as polyamide, polyether block amide, polyethylene, or polyethylene terephthalate or a combination of polymeric and metallic materials may be used to form the penetration member 108.

Furthermore, a lubricious polymeric coating may be applied to the inner and/or the outer surface of the penetration member 108 to reduce friction between the penetration member 108 and the guide wire 112, and/or between the catheter shaft 102 and the penetration member 108. The lubricious polymeric coating may include suitable low friction materials such as TEFLON®, polyetheretherketone (PEEK), polyimide, nylon, polyethylene, or any other lubricious polymer coatings.

As shown in FIG. 1A, the distal nose 110 may be a flattened structure engaged with and/or extending from the catheter shaft 102 at the distal end 106. The distal nose 110 may include the guide wire lumen 120 extending through a flattened portion 122 (shown as wings 122A-122B). The flattened portion 122 may extend the surface area of the distal nose 110 in a plane including the longitudinal axis of the distal nose 110, running along the length of the distal nose 110. In addition, the flattened portion 122 may facilitate in maintaining the orientation of the distal nose 110 parallel to the true lumen of a blood vessel during use as well as rotational orientation of the distal nose 110 such that the guide wire port 116 may be oriented toward the lumen of a blood vessel when deflected.

The guide wire lumen 120 may be a hollow tubular structure that may allow passage of the guide wire 112 and/or the penetration member 108 therethrough and distally beyond the distal nose 110 into a blood vessel where the catheter 100 may be used. The guide wire lumen 120 may be configured with any suitable shape such as circular, oval, polygonal, or irregular. The guide wire lumen 120 may have cross-sectional dimensions greater than the cross-sectional dimensions of the guide wire 112 or the penetration member 108. Further, the cross-sectional dimensions of the guide wire lumen 120 may be less than the thickness of the blood vessel wall where the subintimal recanalization catheter 100 may be used.

In the present embodiment, the flattened portion 122 includes two wings 122A-122B attached to the guide wire lumen 120. The wings 122A-122B may extend in opposite directions from the guide wire lumen 120. The wings 122A-122B may be rectangular, circular, oval, regular, or irregular-shaped members attached to the guide wire lumen 120 in a plane including the longitudinal axis of the guide wire lumen 120. The wings 122A-122B may be thicker near the guide wire lumen 120 and may taper regularly or irregularly towards the edges. Alternatively, the wings 122A-122B may be thicker at the edges and may taper towards the guide wire lumen 120. The wings 122A-122B may have a curvature extending outwardly from the plane including the longitudinal axis of the guide wire lumen 120 in either the same or opposing directions. Furthermore, the wings 122A-122B or portions thereof may be flexible or adapted for flexure. The wings 122A-122B may flex in a vessel wall to adapt to the shape of the vessel wall and follow the curvature of the vessel wall.

Figure 2:
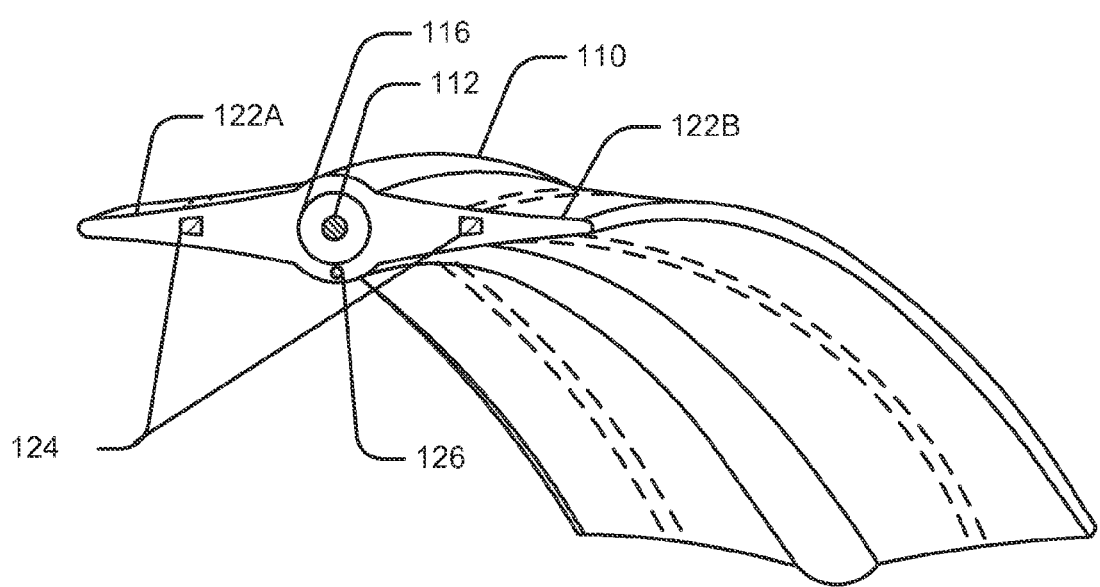
FIG. 2 is an exemplary cross sectional view of the catheter apparatus taken across the plane 2-2.

FIG. 2 illustrates the cross section of the distal nose 110 taken across the plane 2-2. As disclosed, in some embodiments, the wings 122A-122B may possess flexibility to adapt to the shape of a vessel wall. In some circumstances, one or more reinforcing members may be included within the wings 122A-122B. The reinforcing members may facilitate the wings 122A-122B in adapting to the shape of the vessel wall, and they may further prevent the wings 122A-122B from flexing or bending into undesired shapes. Some exemplary reinforcing members may be metallic ribbons, braids, or wires. For example, as shown in FIG. 2, some embodiments may employ reinforcing strips 124 for shaping the distal nose 110. The strips 124 may run parallel to the elongate axis of the distal nose 110, and each wing 122A or 122B may include only one of the strips 124 or more than one of the strips 124. The strips 124 may be of any suitable dimensions that may fit into the wings 122A-122B. The strips 124 may allow the wings 122A-122B to flex into certain shapes, such as, the shape of the vessel wall. In addition, the strips 124 may prevent the wings 122A-122B from flexing into shapes that may hinder or obstruct the movement of the distal nose 110 within the vessel wall. The strips 124 may be made up of any polymeric or metallic materials such as stainless steel, nitinol, or polyamides to provide strength and stability to the wings 122A-122B. In some embodiments, as shown in FIG. 2, the strips 124 may be metallic ribbons passing through a central portion of each wing 122A-122B.

The wings 122A-122B may have dimensions suitable to separate and slide between the adventitia and intima layers of the desired blood vessel where the subintimal recanalization may be conducted. For example, the span of the wings 122A-122B may be less than the circumference of the vessel wall. Moreover, the thickness of the wings 122A-122B may be less than the thickness of the vessel wall, in some instances.

Figure 3A:
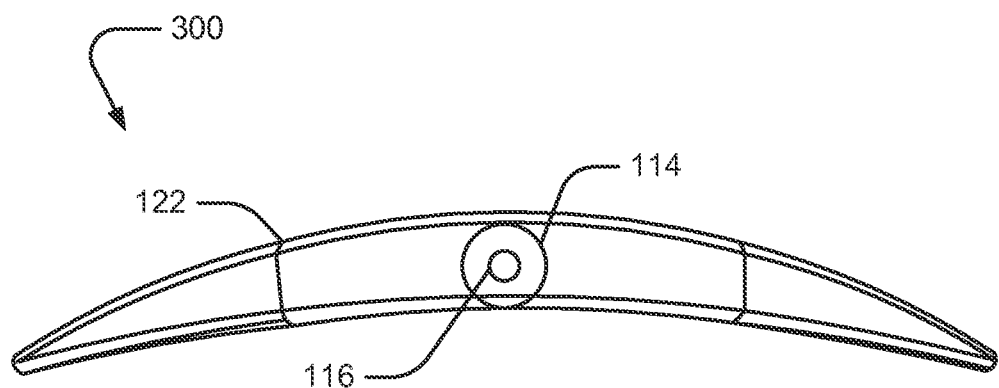
FIGS. 3A-3B illustrate an alternative embodiment of the distal nose of the catheter.
Figure 3B:
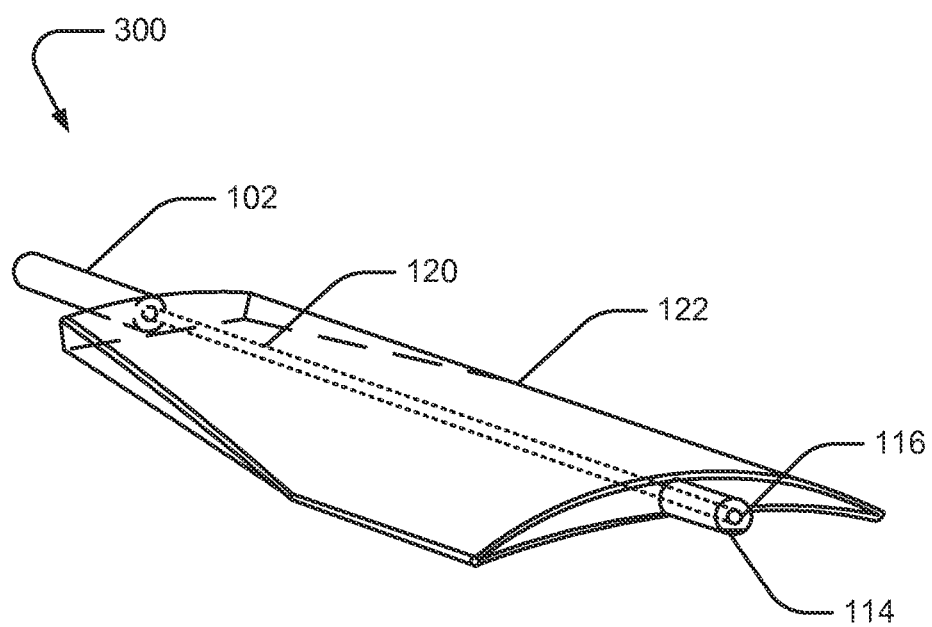

FIGS. 3A-3B exhibit an alternative embodiment 300 of the distal nose (shown as distal nose 110 in FIG. 1A), where FIG. 3A illustrates a cross sectional view of the distal nose 300, and FIG. 3B exhibits a perspective view of the distal nose 300. In this embodiment, the flattened portion 122 is a paddle- or spatula-shaped member that includes the guide wire lumen 120. It may be noted that a person of ordinary skill in the art may envision many other embodiments for the flattened portion 122 capable of achieving the intended purpose in the intended environment. In general, the flattened portion 122 may be any member attached to or formed with the catheter shaft 102 that may increase the surface area of the distal nose 300 (also show as distal nose 110 in FIG. 1A) in a plane including the longitudinal axis of the distal nose 300.

The distal tip 114 of the distal nose 110 may be a blunt or atraumatic tip shaped to prevent any inadvertent damage to a vessel walls upon contact with the distal tip 114. The distal tip 114 may assume any atraumatic shapes such as a blunt ball nose or a beveled or curved nose structure capable of achieving the intended purpose in the intended environment. Further, as discussed above in FIG. 1A, the distal tip 114 may include the guide wire port 116 that may connect to the guide wire lumen 120 to extend the guide wire 112 distally beyond the distal tip 114.

The distal nose 110 may be detachably connected, permanently coupled, or formed as an integral component of the catheter shaft 102. Distal nose 110 may be coupled to distal end 106 by any suitable coupling mechanism, such as assemblies joined by welding, molding, a snap fit, screw fit, luer-lock, or other known attachment mechanisms capable of achieving the intended purpose in the intended environment. Suitable permanent coupling methods may include adhesive bonding, molding, or welding, depending on the distal nose 110 and/or catheter shaft 102 material. Alternatively, distal nose 110 may be formed integral with the distal end 106 of the catheter shaft 102.

The distal nose 110 may be made up of any suitable biocompatible material. For example, polymeric materials such as polyamide, polyetherblockamide, polyethylene, or polyethylene terepthalate may be used to make the distal nose 110. Alternatively, the distal nose 110, or portions thereof, may be made up of metallic materials such as stainless steel or nitinol, or a combination of polymeric and metallic materials. Further, in some embodiments, the guide wire lumen 120 and the wings 122A-122B may be made up of different material, attached during manufacture. In other embodiments, the wings 122A-122B may be detachable from the guide wire lumen 120. Furthermore, in some embodiments, the guide wire lumen 120 and the wings 122A-122B may be formed as a single integral component.

A lubricious polymeric coating may be used at the inner and/or the outer surface of the distal nose 110 to reduce friction between the guide wire lumen 120 and the guide wire 112, and between the vessel walls and the wings 122A-122B. The lubricious polymeric coating may include suitable low friction materials such as TEFLON®, polyetheretherketone (PEEK), polyimide, nylon, polyethylene, or any other lubricious polymer coatings.

As described, the guide wire 112 is a wire on which the catheter 100 may be configured to move forward for delivery to a remote distal location. The guide wire 112 may be a metallic or polymeric wire and/or a stylet. In some embodiments, the guide wire 112 may be made up of biocompatible materials such as stainless steel or nitinol. The dimensions of guide wire 112 may depend on the application of the guide wire 112. For example, the length of the guide wire 112 may depend on the length of the catheter 100, the target location within the vasculature, and the extent to which the guide wire 112 may need to extend beyond the distal tip 114. In addition, the diameter of the guide wire 112 may be less than the cross sectional dimensions of the penetration member 108 and/or the guide wire lumen 120 for insertion into the catheter 100.

The embodiments of the present disclosure may include a deflection mechanism. The deflection mechanism may be any mechanism that may deflect the distal nose 110 and/or the penetration member 108 towards the true lumen of a blood vessel when the distal nose 110 is present in the subintimal space of the vessel wall. As shown in FIGS. 1B-C, the present embodiment of the disclosure illustrates the use of a pull wire 126 as a deflection mechanism to deflect the distal nose 110 towards the true lumen of a blood vessel in a subintimal space. The pull wire 126 may be disposed within the catheter shaft 102 extending from the proximal end 104 to the distal end 106 (shown in FIG. 1A) and through the distal nose 110 (shown in FIG. 1A). The pull wire 126 may be positioned ventrally, below the guide wire lumen 120. The wings 122A-122B of the flattened portion 122 may ensure proper rotational orientation such that the pull wire 126 is positioned between the guide wire lumen 120 and the lumen of a blood vessel. In addition, the pull wire 126 may be connected to any mechanism that may exert actuation and/or tension proximally on the pull wire 126 to deflect the distal nose 110. For example, as shown in FIG. 1B, a rotatable knob 128 attached to the pull wire 126 as a pull mechanism may be used. Alternatively, the embodiment 100C shown in FIG. 1C may include a slidable button 130 connected to the proximal end of the pull wire 126. It may be noted that the pull mechanisms 128, 130 illustrated in the disclosure are merely exemplary, and a person skilled in the art may utilize one of many suitable pull mechanisms known in the art to actuate (push or pull) the pull wire 126 capable of achieving the intended purpose in the intended environment.

Further, dimensions and construction of pull wire 126 may be tailored to specific environments. For example, the pull wire 126 may have a length suitable to extend from the distal tip 114 to the proximal end 104. In addition, the diameter of the pull wire 126 may be large enough to provide the necessary strength to the pull wire 126 that may be required to deflect the distal nose 110.

Figure 4A:
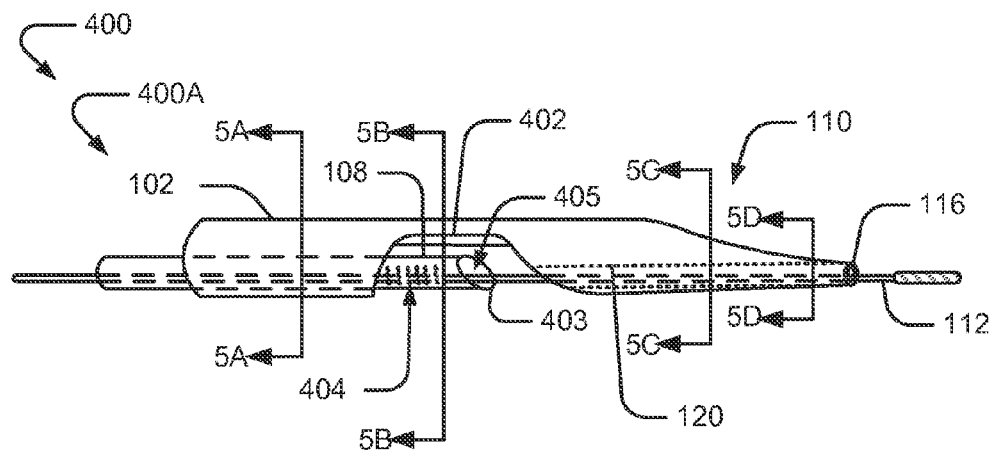
FIGS. 4A-4B illustrate another embodiment of a subintimal recanalization catheter.
Figure 4B:
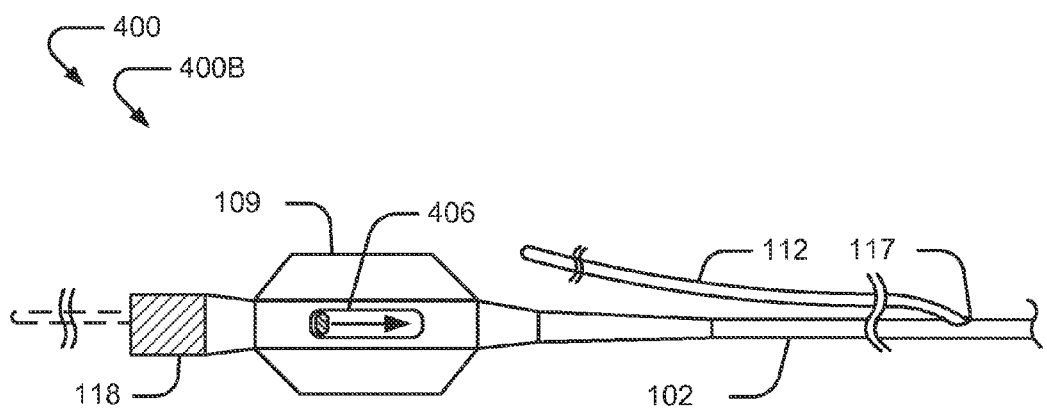

Another embodiment of a re-entry catheter is illustrated in FIGS. 4A-4B, a catheter 400 including a distal portion 400A, shown in FIG. 4A, and a proximal portion 400B, shown in FIG. 4B. As shown in FIG. 4A, the distal portion 400A may include an opening 402 located proximally to the distal nose 110 near the distal end 106. In addition, the penetration member 108 may not extent into or through the guide wire lumen 120 of the distal nose 110, and the opening 402 may expose the distal end of the penetration member 108. However, the distal tip 403 of the penetration member 108 may be positioned proximal to the distal nose 110 co-axially aligned to the guide wire lumen 120. Further, in an OTW design, the guide wire 112 may extend through the penetration member 108 to the guide wire lumen 120 via a port 405 located at the distal tip 403.

In some embodiments, the penetration member 108 may be considered as a deflectable re-entry or redirection tube and may deflect away from the central axis of the catheter shaft 102 to extend out of the opening 402. In that instance, the deflected penetration member 108 may aid the guide wire 112 to puncture and penetrate the intima layer of a blood vessel. In some instances, the penetration member 108 may include flexibility characteristics permitting the penetration member 108 to be deflectable away from the catheter shaft 102 into a curved or bent configuration. In other instances, the penetration member 108 may include one or more cuts or slits 404 formed through the sidewalls of the penetration member 108, providing the penetration member 108 with a degree of lateral flexibility capable of achieving the intended purpose in the intended environment. For example, the penetration member 108 may include a helical cut or slit 404 formed through the sidewalls of the penetration member 108. The helical cut or slit 404 may extend partially around the circumference of the penetration member 108 along a length of the penetration member 108, or another arrangement of cuts or slits 404 may be formed in another fashion to provide a desired degree of flexibility capable of achieving the intended purpose in the intended environment. In some embodiments, the penetration member 108 may be formed from a hypo-tube using a laser, water jet, or any other cutting mechanisms used to form the cuts or slits 404 on the surface thereof. In some other embodiments, the penetration member 108 may be manufactured with cuts and slits 404 using 3D printing technologies.

In some embodiments, the proximal portion 400B shown in FIG. 4B may include an actuation device 406 that may facilitate an operator to actuate the penetration member 108 relative to the catheter shaft 102, to deflect the penetration member 108 towards the intima layer. The actuation device 406 may be an electronic or mechanical switch, a rotatable knob, push button, lever or other actuation mechanisms. Some exemplary deflection mechanisms are discussed in detail with FIGS. 9A-9B and 10A-10B below.

Figure 5A:
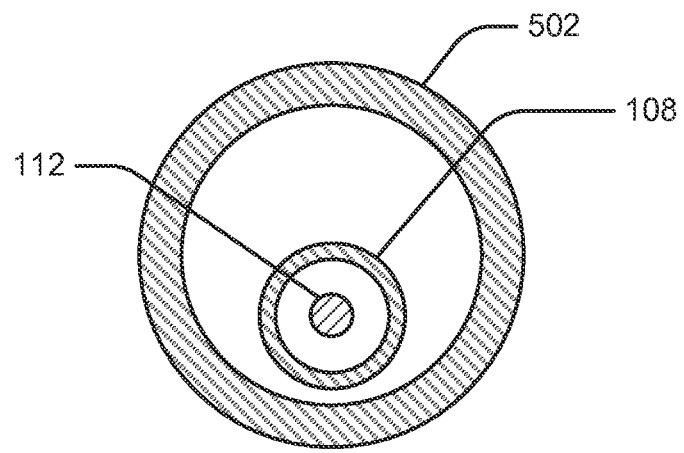
FIGS. 5A-5D illustrate cross-sectional views of the exemplary catheter shown in FIG. 4 taken along planes 5A-5A, 5B-5B, 5C-5C, and 5D-5D respectively.

FIGS. 5A-5D illustrate cross-sectional views of the distal portion 400A shown in FIG. 4A taken along the planes 5A-5A, 5B-5B, 5C-5C, and 5D-5D respectively. In some embodiments, as shown in FIG. 5A, the catheter shaft 102 or a portion thereof may include an outer tubular member 502 representing a cross section of the catheter shaft 102 across plane 5A-5A. The penetration member 108 may extend through the lumen of the outer tubular member 502, and the guide wire 112 may extend through the lumen of the penetration member 108.

Figure 5B:
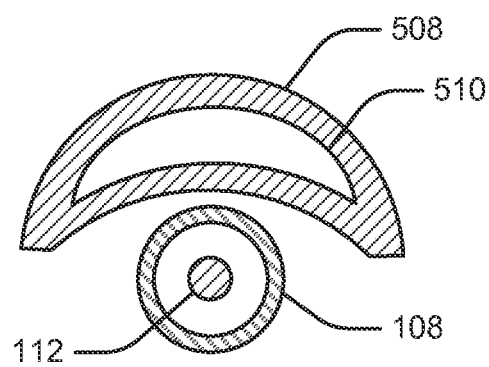

As discussed, FIG. 5B illustrates a cross section of the distal portion 400A shown in FIG. 4A taken along plane 5B-5B. In some embodiments, as shown in FIG. 5B, the catheter shaft 102 (shown in FIG. 4A) or a portion thereof may include a crescent-shaped or "D" or "U"-shaped portion 508 including a lumen 510. The penetration member 108 may extend exterior to and below the crescent-shaped or "D"-shaped portion 508 running parallel to the crescent-shaped or D-shaped portion 508. The guide wire 112 may extend through the lumen of the penetration member 108. Referring to FIGS. 4A and 5B, the crescent-shaped or D-shaped portion 508 may define a cross section of the distal portion 400A across the plane 5B-5B passing through the opening 402. Similarly, in some embodiments the lumen 510 may provide a path to extend the guide wire 112 to the guide wire lumen 120 in the distal nose 110. As shown, the crescent-shaped or D-shaped portion 508 may not restrict the penetration member 108 from moving towards the region opposite to the crescent-shaped or D-shaped portion 508.

Figure 5C:
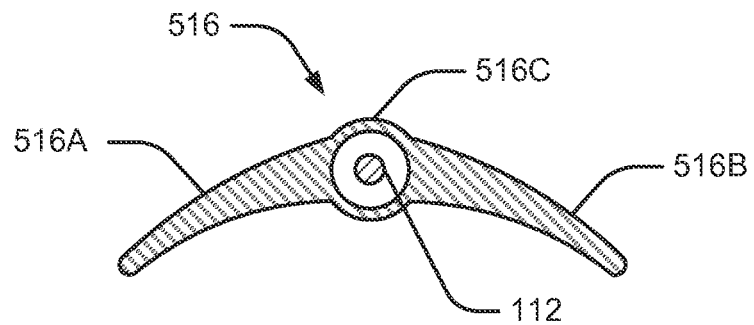

As discussed, FIG. 5C illustrates a cross section of the distal portion 400A as shown in FIG. 4A taken along plane 5C-5C. In some embodiments, as shown in FIG. 5C, the distal nose 110 (shown in FIG. 4A) or a portion thereof may include a winged tubular portion 516 with the guide wire 112 passing through the lumen of the winged tubular portion 516. The winged tubular portion 516 may include two wing-shaped structures 516A and 516B extending in opposite directions from a tubular portion 516C.

Referring to FIGS. 4A and 5C, the winged tubular portion 516 may define a cross section of the distal nose 110 across the plane 5C-5C shown in FIG. 4A. Similarly, the tubular portion 516C may define a cross section of the guide wire lumen 120 and the two wing-shaped structures 516A-516B may describe wings 122A-122B of the distal nose 110.

Figure 5D:
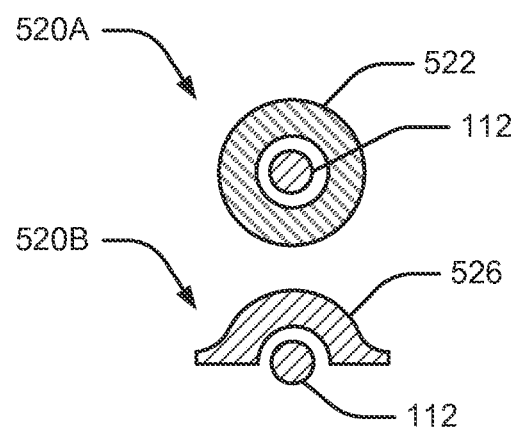

As discussed, FIG. 5D illustrates a cross section of the embodiment of FIG. 4A taken along the plane 5D-5D. FIG. 5D illustrates two exemplary alternative embodiments 520A and 520B of a portion of the distal nose 110 near the distal tip 114. As shown, the embodiment 520A may include a tubular portion 522 and the guide wire 112 extending through the tubular portion 522. Referring to FIGS. 4A and 5D, the tubular portion 522 may define a cross section of the guide wire lumen 120 across the plane 5D-5D shown in FIG. 4A. Similarly, the embodiment 520B may include a crescent-shaped or D-shaped portion 526 defining cross sections of the guide wire lumen 120 along with the guide wire 112 extending through the crescent-shaped or D-shaped portion 526. The embodiment 520A exhibits that the guide wire lumen 120 may be a closed channel near the distal tip 114, while the embodiment 520B exhibits that the guide wire lumen 120 may be an open channel.

Figure 6A:
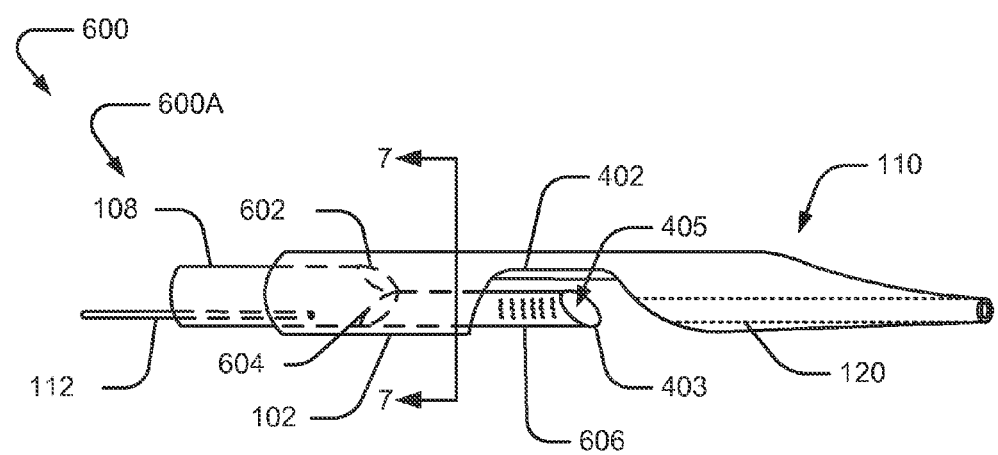
FIGS. 6A-6B exhibit another alternative embodiment of a subintimal recanalization catheter.
Figure 6B:
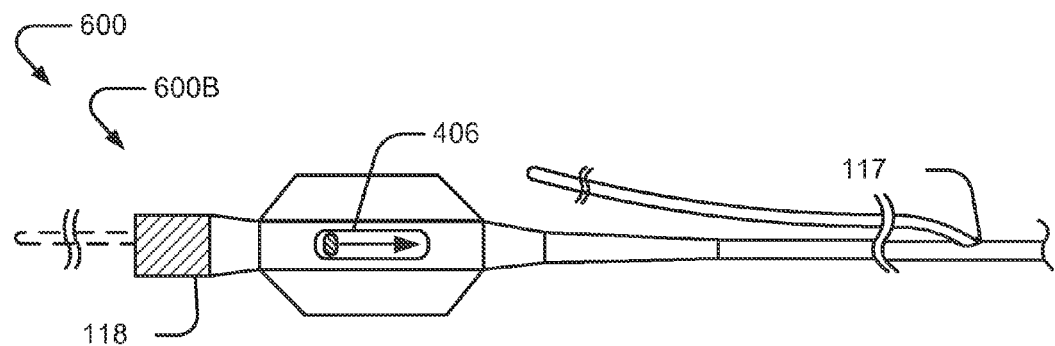

FIGS. 6A-6B exhibit another alternative embodiment of the present disclosure. FIG. 6A exhibits a distal portion 600A and FIG. 6B depicts a proximal portion 600B of a catheter 600. As shown in FIG. 6A, the penetration member 108 may include two or more ports 602 and 604 at a location proximate to the proximal end of the opening 402. The ports 602 and 604 are discussed further with FIG. 7. Furthermore, a distal portion 606 of the penetration member 108 may extend from the port 604 towards the opening 402 such that the distal tip 403 of the distal portion 606 may lie proximal of the proximal end of the distal nose 110 within the opening 402. In some embodiments, for example, embodiments similar to the embodiment shown in FIGS. 1A-C, the distal portion 606 may engage with the guide wire lumen 120 by allowing the guide wire 112 to extend to the guide wire lumen 120 through port 405. In some other embodiments, the distal portion 606 may flex away from the longitudinal axis of the catheter shaft 102 through opening 402 directing the port 405 towards a vessel lumen (not shown). Further, the proximal portion 600B of catheter 600 shown in FIG. 6B may be similar to the proximal portion 400B of catheter 400 shown in FIG. 4B.

Figure 7:
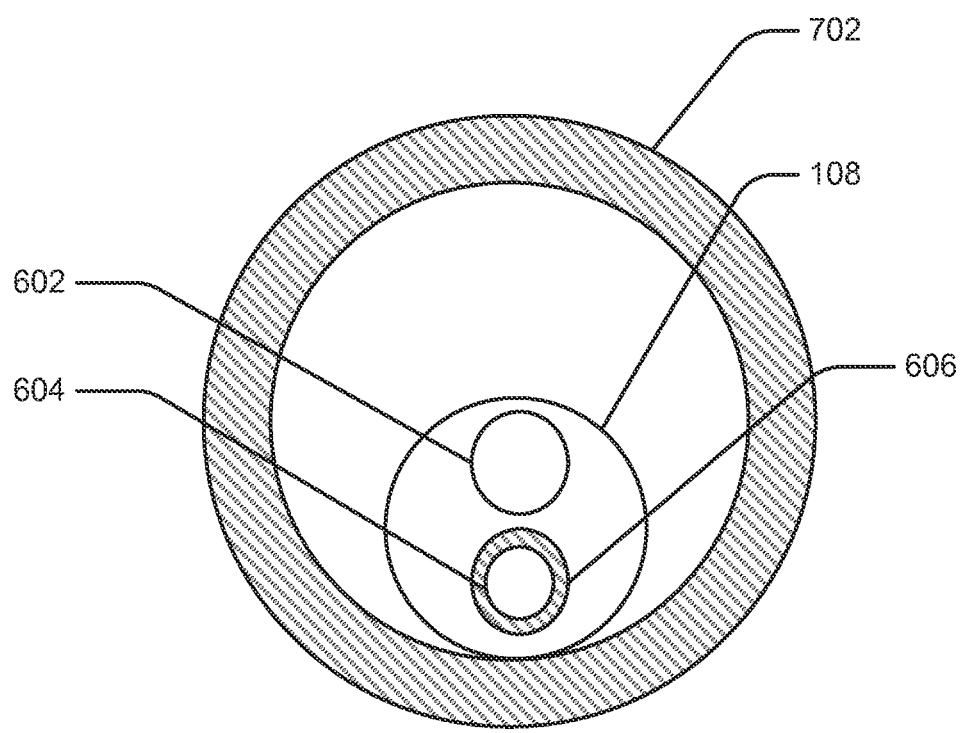
FIG. 7 is an exemplary cross-sectional view of the catheter of FIG. 6A taken along plane 7-7.

FIG. 7 is a cross-sectional view of the distal portion 600A shown in FIG. 6A taken along plane 7-7. As shown in FIG. 7, the catheter shaft 102 or a portion thereof may include an outer tubular member 702 defining the cross section of the catheter shaft 102 and the penetration member 108 extending through the outer tubular member 702. The ports 602 and 604 may connect to the lumen of the penetration member 108. The ports 602 and 604 may allow the operator to extend the guide wire 112 through alternative routes within the catheter 600. The alternative routes to extend the guide wire 112 are described below along with FIGS. 8A-8B.

Figure 8A:
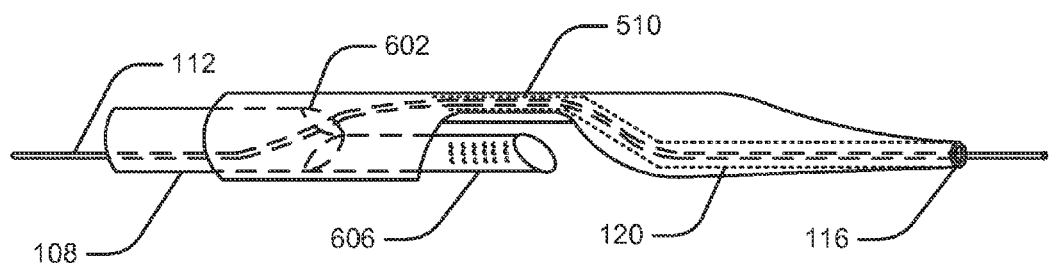
FIGS. 8A-8B illustrate two alternative routes for the guide wire within the embodiment of the catheter shown in FIG. 6A.
Figure 8B:
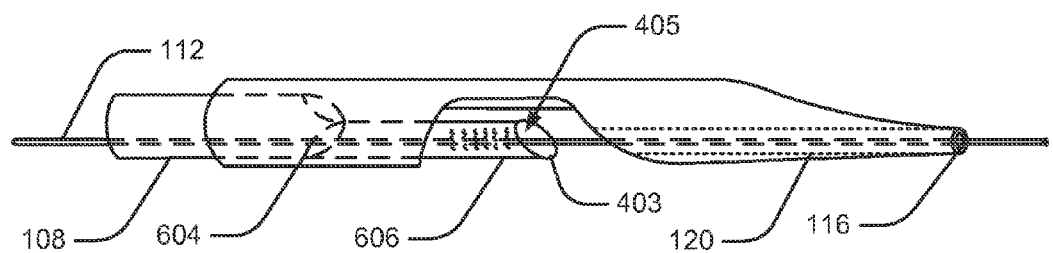

As described, FIGS. 8A-8B illustrate alternative routes for the guide wire 112 within the distal portion 600A of catheter 600 shown in FIG. 6A. As shown in FIG. 8A, the operator may route the guide wire 112 from the penetration member 108 through port 602, lumen 510, and guide wire lumen 120 through the distal nose 110 to the guide wire port 116. Alternatively, as shown in FIG. 8B, the operator may route the guide wire 112 from within the penetration member 108 through port 604, distal portion 606, port 405 and guide wire lumen 120 through the distal nose 110 to the guide wire port 116.

This feature of alternative routes may allow the operator to use the penetration member 108 to deflect towards the true lumen of a blood vessel within the vessel wall, which in turn may facilitate in subintimal re-entry through port 405. For example, if the guide wire 112 is routed through the route shown in FIG. 8B, the distal portion 606 of the penetration member 108 may not deflect as the guide wire 112 may obstruct deflection. However, if the guide wire 112 is routed through the route shown in FIG. 8A, the distal portion 606 may be free to deflect away from the central axis of the catheter shaft 102 and may direct the port 405 towards the true lumen of a blood vessel within the vessel wall. After deflection, the guide wire 112 may be re-routed through the distal portion 606 and port 405 towards the vessel lumen. Many mechanisms, such as motors, hydraulics, strings, or shafts or other mechanisms capable of achieving the intended purpose in the intended environment may be used to deflect the distal portion 606.

The following sections elaborate on some of the exemplary mechanisms to deflect the distal portion 606. It may be noted that in some embodiments such as the embodiment shown in FIG. 4A, the penetration member 108 may not contain the ports 602 and 604. In such embodiments, the deflection mechanisms may deflect the entire penetration member 108. Furthermore, a person skilled in the art may appreciate that other embodiments may have a different deflection portion of the penetration member 108 and the deflection process may deviate from the exemplary process described in the following sections.

Figure 9A:
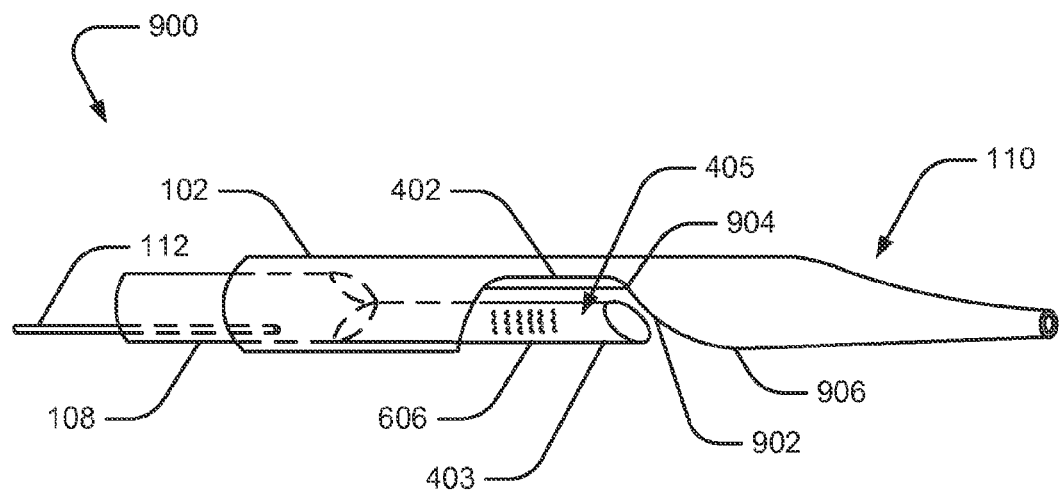
FIGS. 9A-9B illustrate an exemplary deflection mechanism to deflect the penetration member towards the vessel lumen.
Figure 9B:
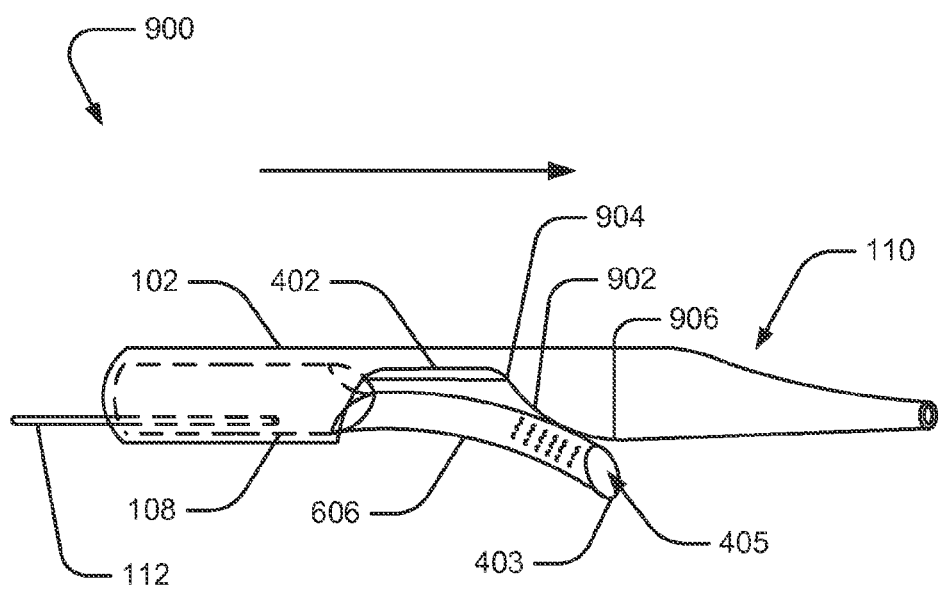

As discussed, FIGS. 9A-9B illustrate an exemplary deflection mechanism to deflect the penetration member 108 or its distal portion 606 towards the vessel lumen. FIG. 9A depicts a distal portion of a catheter 900 with the penetration member 108 in a non-deflected position. FIG. 9B depicts the distal portion of the catheter 900 with the penetration member 108 in a deflected position. The catheter 900 may be similar to the catheter 600 shown in FIGS. 6A-6B, and may include an additional component, a ramp 902 as a deflection mechanism.

As shown in FIG. 9A, the ramp 902 may be a portion of or affixed on the distal nose 110 at the distal portion of the opening 402 having a slant running from its proximal end 904 near the central axis of the catheter shaft 102 to its distal end 906 at the edge of the catheter shaft 102. In addition, the ramp 902 may lie in a straight line with the central axis of the penetration member 108, in some instances.

Referring to FIG. 9B, in some embodiments, an actuation means such as the actuation device 406 shown in FIGS. 4B and 6B may actuate the penetration member 108 to move distally towards the ramp 902 to effectuate the deflection process. Due to this distal motion, the distal portion 606 of the penetration member 108 may hit the ramp 902 near the proximal end 904 and may deviate towards the distal end 906 along the slant of the ramp 902. This deviation may in turn deflect the distal portion 606 away from the central axis of the catheter shaft 102. Alternatively, in some embodiments, the actuation device 406 may actuate the distal nose 110 to move proximally along the central axis of the catheter shaft 102.

Figure 10A:
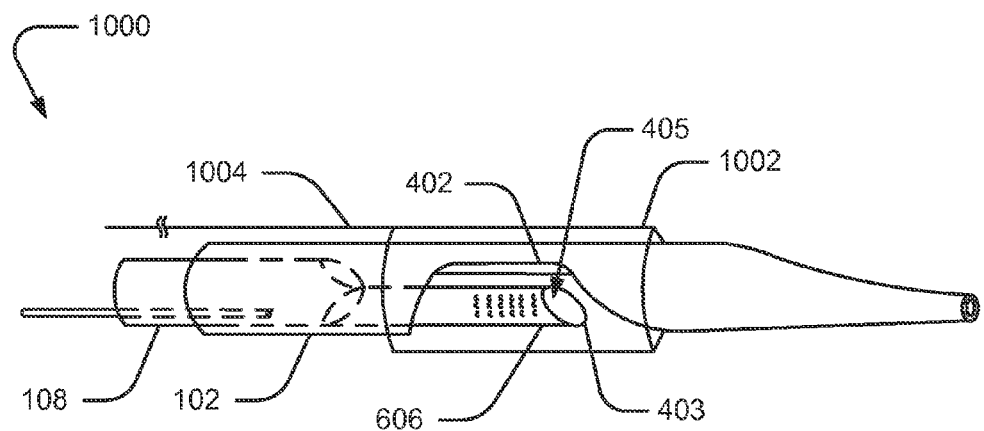
FIGS. 10A-10B depict another exemplary deflection mechanism to deflect the penetration member towards the vessel lumen.
Figure 10B:
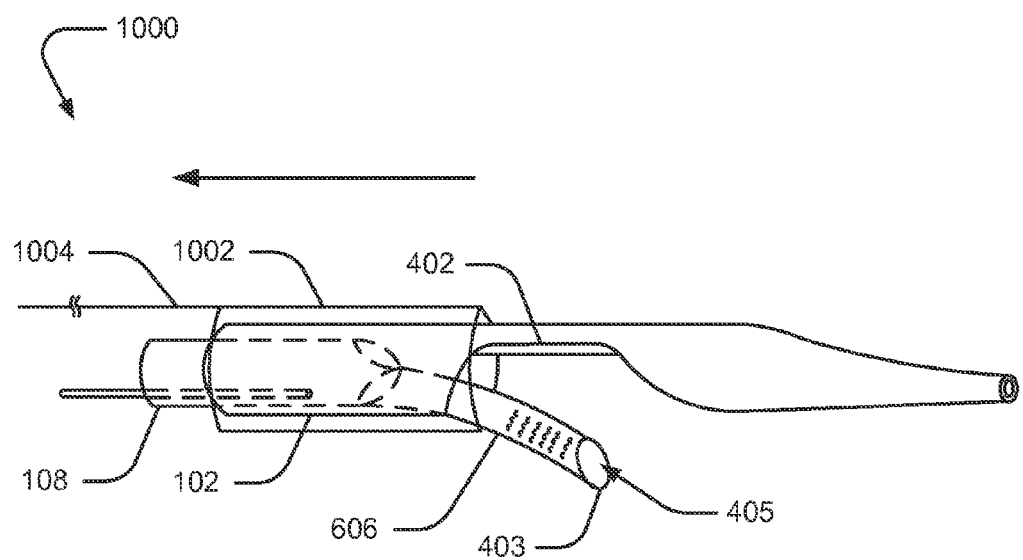

FIGS. 10A-10B illustrate another exemplary deflection mechanism for deflecting the penetration member 108 or its distal portion 606 towards the vessel lumen. FIG. 10A depicts a distal portion of the catheter 1000 with the penetration member 108 in a non-deflected position. FIG. 10B exhibits the distal portion with the penetration member 108 in a deflected position. The catheter 1000 may be similar to the catheter 600 shown in FIGS. 6A-6B, and may include an actuable sleeve 1002 as a deflection mechanism.

In some embodiments, the penetration member 108 may be configured to be curved or deflected from a generally axially aligned configuration. In an equilibrium configuration, the penetration member 108 may extend from parallel to the catheter shaft 102 to a curved configuration in which the distal portion 606 of the penetration member 108 is curved away from the longitudinal axis of the catheter shaft 102. For example, the distal portion 606 may be manufactured with a curvature or a bent structure such that the distal portion 606 when not constrained by the sleeve 1002 may automatically reconfigure to a curved position. In such embodiments, a mechanism to selectively hold and release the pre-curved distal portion 606 within the catheter shaft 102 may be required. FIGS. 10A-10B illustrate one such mechanism using the sleeve 1002 to constrain the distal portion 606 in a straightened configuration.

As illustrated in FIG. 10A, the actuable sleeve 1002 may be a sheath covering the catheter shaft 102 over the region of the opening 402. The sleeve 1002 may act as constraint to prevent the distal portion 606 from deflecting away from the central axis of the catheter shaft 102. The sleeve 1002 may be shaped such that it may extend over the catheter shaft 102. In addition, the sleeve 1002 may be made up of any metallic or polymeric material that may have enough strength to hold the curved distal portion 606 within the catheter shaft 102.

Referring to FIG. 10B, in some embodiments an actuation means such as the actuation device 406 shown in FIGS. 4B and 6B may actuate the sleeve 1002. The actuation device 406 may be connected to the sleeve 1002 using any element such as a wire, a string, or a shaft. In the illustrated embodiment of FIGS. 10A-10B, a wire 1004 may be connected to the sleeve 1002 to actuate it. Upon actuation, the sleeve 1002 constraining the distal portion 606 of the penetration member 108 may move proximally along the central axis of the catheter shaft 102 allowing the distal portion 606 to automatically curve (deflect) away from the central axis of the catheter shaft 102 and out through the opening 402 when unconstrained by the sleeve 1002.

It may be noted that the exemplary mechanisms to deflect the distal portion 606 illustrated herein are merely exemplary and a person of ordinary skill in the art may contemplate many other mechanisms to deflect the sleeve 1002.

Figure 11:
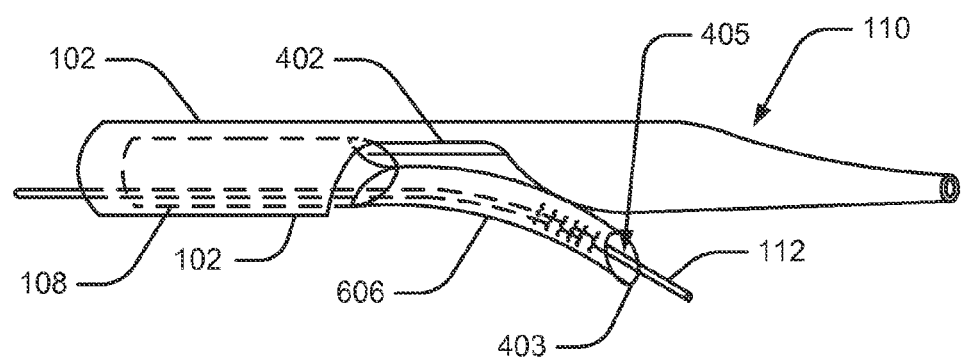
FIG. 11 is a side plan view of the embodiment of the catheter shown in FIGS. 6A-6B with the distal end of the penetration member projected away from the elongate axis of the catheter.

As discussed above in FIGS. 6A and 6B, the deflection of the distal portion 606 or the entire penetration member 108 may assist in re-entering the true lumen of a blood vessel through the inner vessel wall. FIG. 11 illustrates exemplary mechanisms for re-entry using the deflected distal portion 606. In some embodiments, as shown in FIG. 11, the deflected distal portion 606 may route the guide wire 112 towards the true lumen of the vessel through port 405. The guide wire 112 may then be advanced distally out of the distal port of the penetration member 108 and puncture the inner vessel wall to re-enter the true lumen of the vessel. Alternatively, the distal tip 403 of the penetration member 108 may be configured to facilitate piercing and/or dissection of the tissue layers of the blood vessel. For example, the tip 403 may include a sharp, rigid, or piercing feature. In some embodiments, the tip 403 may include an angled distal edge, providing the tip 403 with a sharpened cutting or piercing surface. The tip 403 may puncture the vessel wall and may route the guide wire 112 directly into the vessel lumen. It may be noted that the re-entry mechanisms discussed above are merely exemplary and a person of average skill in the art may contemplate other mechanisms for re-entry into the true lumen of a vessel using the deflected penetration member 108.

Figure 12:
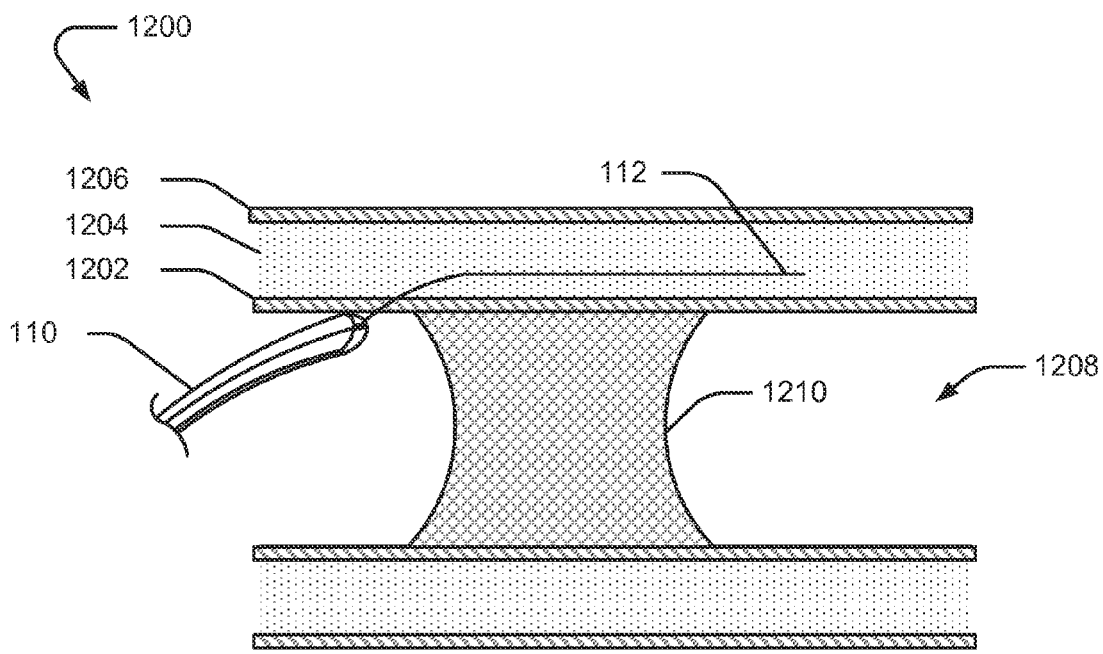
FIGS. 12-16 illustrate aspects of an exemplary method for re-entering the true lumen of an occluded blood vessel using the catheter apparatus of FIGS. 1A-1B.

FIGS. 12-16 illustrate aspects of an exemplary method for re-entering the true lumen of an occluded blood vessel using the catheter 100 of FIGS. 1A-1C. As shown in FIG. 12, a blood vessel 1200 typically has three tissue layers, an innermost layer or intima layer 1202 (tunica intima), an intermediate layer or media layer 1204 (tunica media), and an outermost layer or adventitia layer 1206 (tunica adventitia), with the media layer 1204 positioned between the intima layer 1202 and the adventitia layer 1206. The intima layer 1202 is a layer of endothelial cells lining the lumen 1208 of the vessel 1200, as well as a sub-endothelial layer made up of mostly loose connective tissue. The media layer 1204 is a muscular layer formed primarily of circumferentially arranged smooth muscle cells. The adventitia layer 1206, which forms the exterior layer of the vessel 1200, is made up of loose connective tissue made up of fibroblasts and associated collagen fibers.

In some instances, a chronic total occlusion (CTO) 1210 may block the blood vessel 1200 and may stop the flow of fluids though the vessel lumen 1208. In addition, it may be difficult or impossible to pass through the occlusion 1210 in the lumen 1208 with a medical device to recanalize the vessel 1200. In such instances, it may be possible to recanalize the blood vessel 1200 through a subintimal approach using a device such as, a subintimal recanalization catheter 100 (see FIG. 1).

As shown, the guide wire 112 may initially be moved forward through the lumen 1208 of the vessel 1200 to a location proximate a proximal end of the occlusion 1210, which is blocking the lumen 1208. The guide wire 112 may then be moved forward to penetrate outward through the intima layer 1202 at a location proximate a proximal end of the occlusion 1210 into the wall of the vessel 1200. With the tip of the guide wire 112 located between the intima layer 1202 and the adventitia layer 1206, the guide wire 112 may be further moved distally in a subintimal manner to create a subintimal space between the intima layer 1202 and the adventitia layer 1206. The guide wire 112 may be moved forward in a subintimal manner until the distal tip of the guide wire 112 is located distal of the distal end of the occlusion 1210 in the subintimal space created, such as by dissection of tissue layers of the wall of the vessel 1200.

Figure 13:
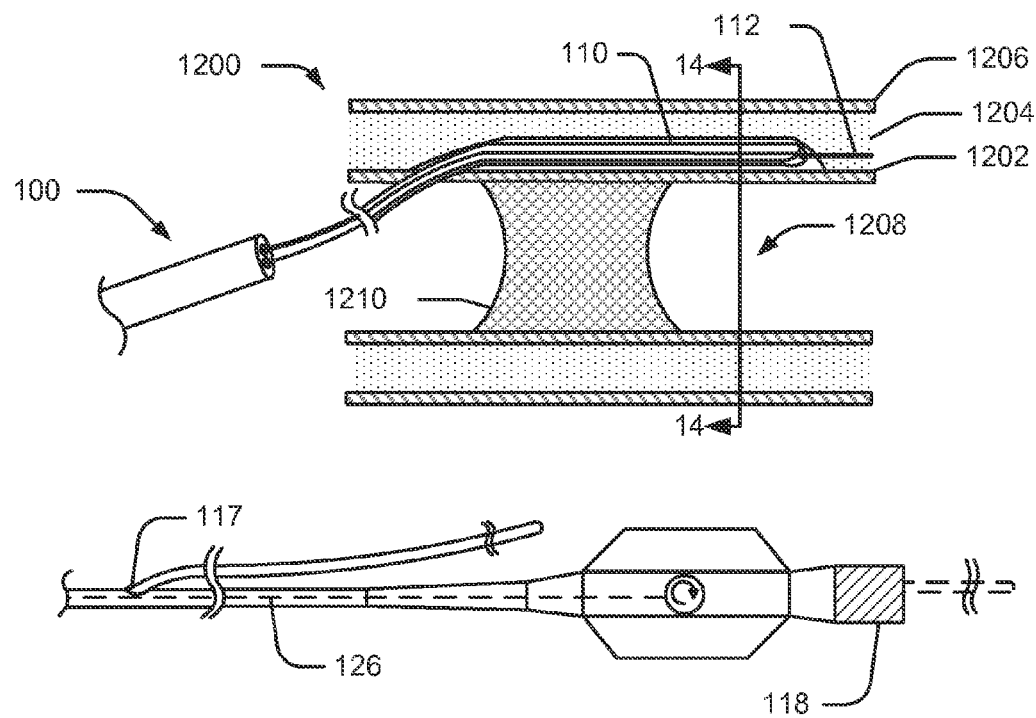

As shown in FIG. 13, the recanalization catheter 100 may then be moved distally over the guide wire 112. The catheter 100 may be moved forward from the true lumen 1208, proximal of the occlusion 1210 into the subintimal space between the intima layer 1202 and the adventitia layer 1206, to a position in the subintimal space in which the distal nose 110 or a portion of it is located distal of the distal end of the occlusion 1210. The catheter 100 may then move forward into the subintimal space parallel to the intima layer 1202 until the catheter 100 or a portion of it approaches the desired position (distal of the distal end of the occlusion 1210).

Figure 14:
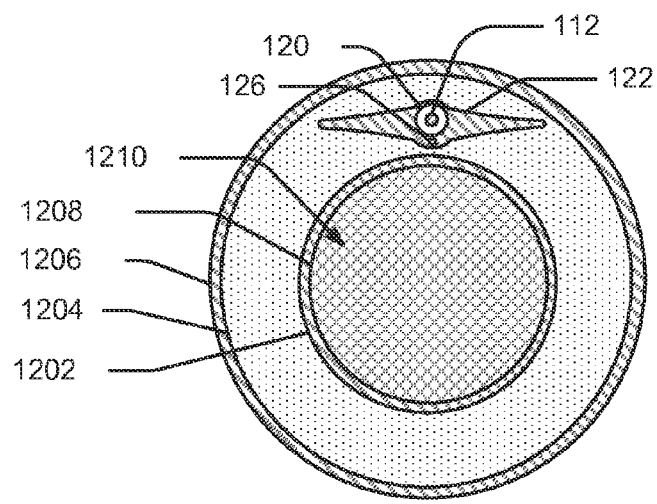

FIG. 14 exhibits a cross section of the distal position of the catheter 100 positioned in the subintimal space created between the tissue layers of the vessel 1200 along the plane 14-14 distal of the occlusion 1210 in FIG. 13. As shown, the vessel 1200 includes three tissue layers 1202, 1204, and 1206 along with the central lumen 1208 having the occlusion 1210. In addition, the cross section of the catheter 100 within the middle tissue layer 1204 includes a winged outer structure 122 representing a cross section of the distal nose 110, showing the guide wire lumen 120 with the guide wire 112 disposed within the guide wire lumen 120. Furthermore, the pull wire 126 is oriented such that the pull wire 126 is located ventrally, below the guide wire lumen 120 within the winged structure 122. Referring to FIGS. 13 and 14, the winged structure 122 (distal nose 110) may aid in providing stability to the catheter 100 (shown in FIG. 13) within the vessel 1200 by fixing the orientation of the catheter 100 parallel to the vessel lumen 1208 in the media layer 1204. Moreover, the parallel orientation of the catheter 100 within the wall of the vessel 1200 may keep the pull wire 126 below the guide wire lumen 120 (radially inward), which in turn may ensure deflecting the distal nose 110 towards the vessel lumen 1208 distal of the occlusion 1210.

Figure 15:
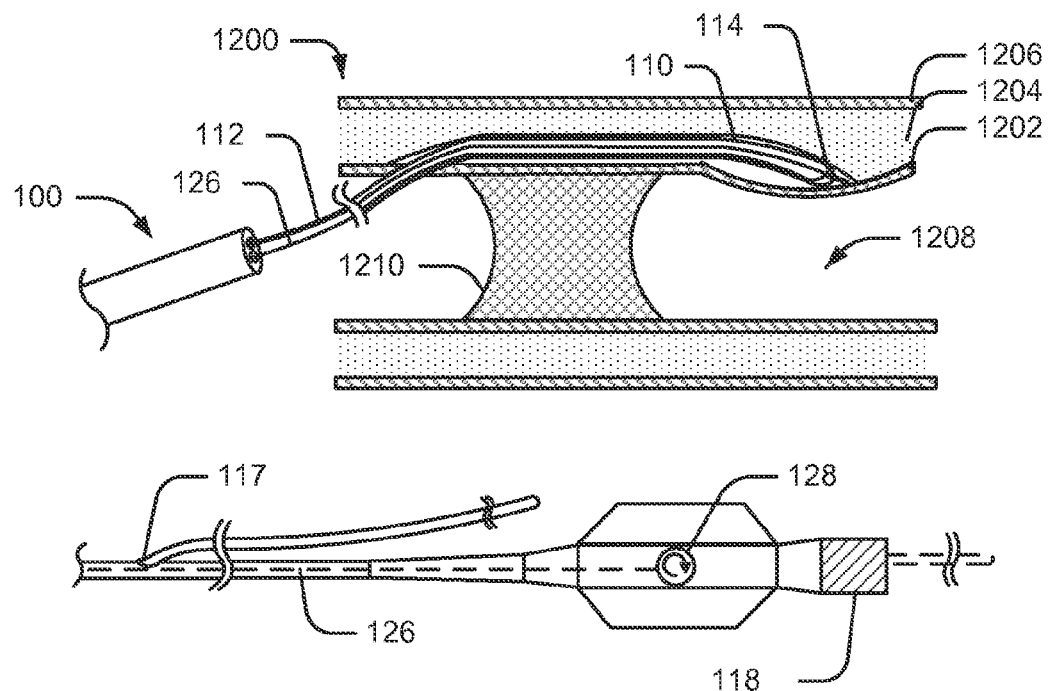

FIG. 15 illustrates the deflection of the distal tip 114 towards the vessel lumen 1208. When the distal nose 110 or a portion of it approaches to a position distal of the occlusion 1210, the operator may actuate the pull mechanism using the knob 128 or slidable button 130 or other actuation member to deflect the distal tip 114. Once the pull wire 126 is pulled, it applies a deflecting force on the distal nose 110 forcing it to curve radially inwards. As the pull wire 126 is disposed at a ventral location within the distal nose 110, the net force (acting on the distal nose 110) curves the distal nose 110 toward the vessel lumen 1208, thereby deflecting the distal tip 114 towards the intima layer 1202.

Figure 16:
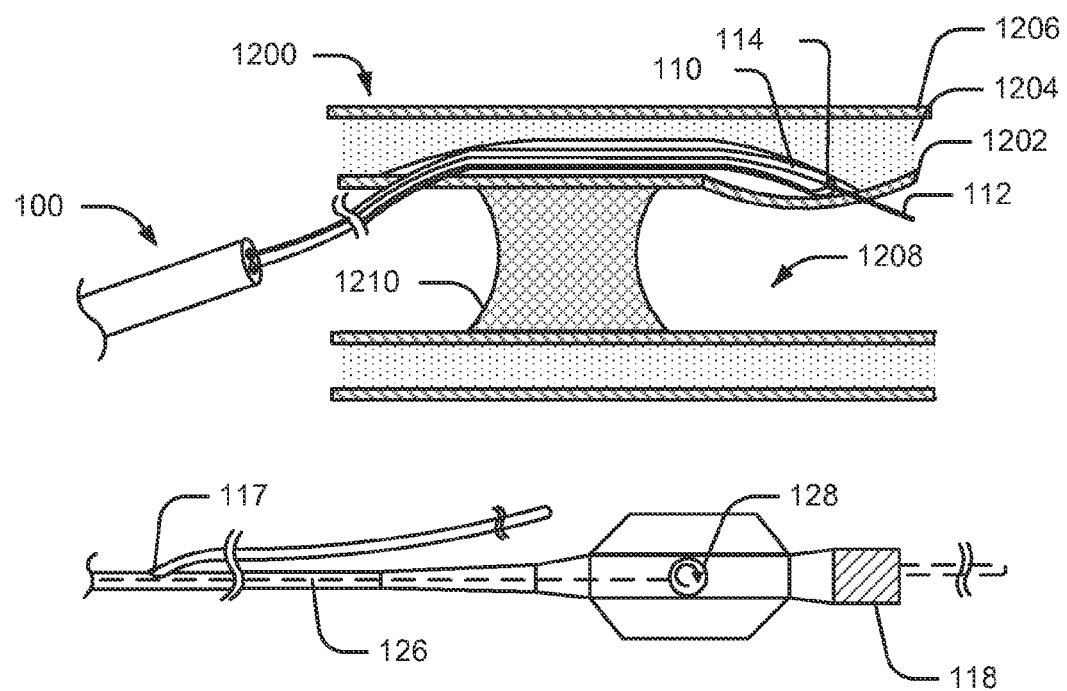

FIG. 16 depicts the guide wire 112 advancing distally from the distal tip 114 and penetrating the intima layer 1202 and re-entering the true lumen 1208 of the vessel 1200. As discussed, the pull wire 126 may deflect the distal tip 114 towards the intima layer 1202, which guides the guide wire port 116 toward the intima layer 1202. The operator may then extend the guide wire 112 distally through guide wire port 116 toward the intima layer 1202. Further, the operator may force the guide wire 112 into the intima layer 1202 to puncture the intima layer 1202 and enter the true lumen 1208 of the vessel 1200. This process may rupture the intima layer 1202 and create a false lumen extending through the subintimal space from the proximal end to the distal end of the occlusion 1210.

Figure 17A:
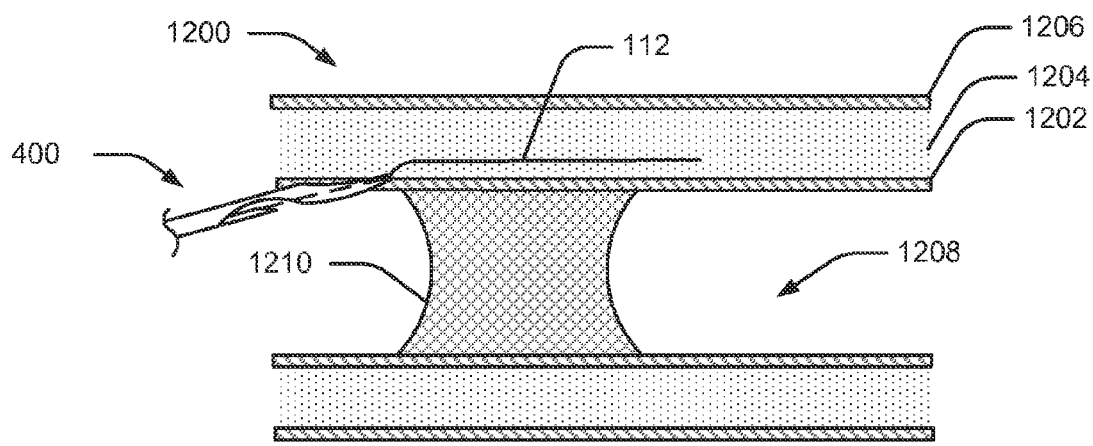
FIGS. 17A-17D illustrate aspects of another exemplary method for re-entering the true lumen of an occluded blood vessel using the catheter apparatus of FIGS. 4A and 4B.

FIGS. 17A-17D illustrate additional aspects of an exemplary method for re-entering the true lumen 1208 of an occluded blood vessel 1200 using the catheter 400 of FIGS. 4A and 4B or catheter 600 of FIGS. 6A and 6B. Similar to the method illustrated in FIGS. 12-16, as shown in FIG. 17A, the guide wire 112 may initially move forward through the lumen 1208 and penetrate outward through the intima layer 1202 at a location proximate a proximal end of the occlusion 1210 into the vessel 1200. The guide wire 112 may then be advanced through the subintimal space to a location distal of the distal end of the occlusion 1210.

Figure 17B:
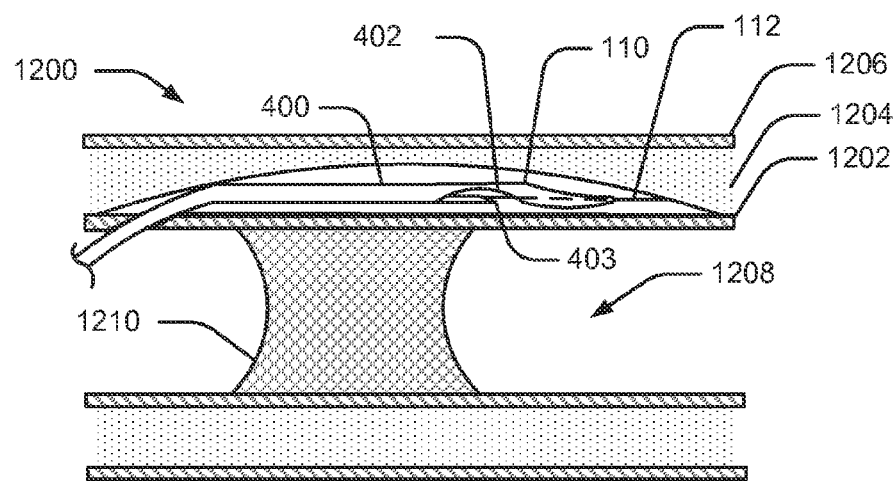

Further, as shown in FIG. 17B, the catheter 400 may then be advanced distally over the guide wire 112 from the true lumen 1208, proximal of the occlusion 1210 into the subintimal space, to a position where the distal nose 110 and the opening 402 is located distal of the distal end of the occlusion 1210.

Figure 17C:
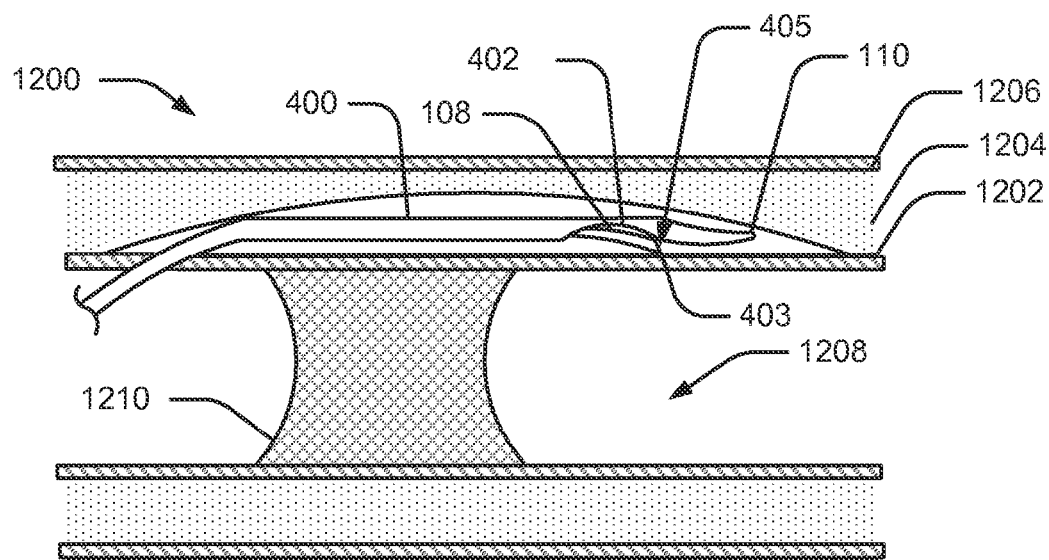

As illustrated in FIG. 17C, once the opening 402 approaches the distal end of the occlusion 1210, the operator may use any suitable deflection mechanism to deflect the penetration member 108 toward the lumen 1208. For example, the deflection mechanisms described in FIGS. 9A-9B and 10A-10B may be used to deflect the penetration member 108 or its distal portion 606 to deflect and position the port 405 towards the intima layer 1202 through the opening 402. For example, the operator may advance the penetration member 108 distally against the ramp 902 to deflect the penetration member 108.

Figure 17D:
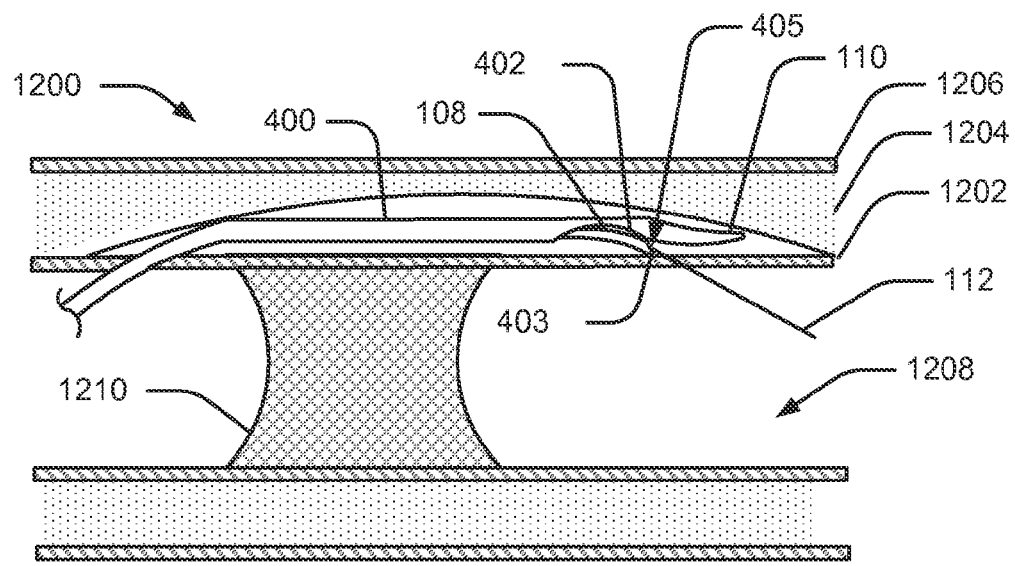

FIG. 17D illustrates the guide wire 112 penetrating the intima layer 1202. After deflection, the penetration member 108 may route the guide wire 112 through port 405 towards the intima layer 1202, as illustrated in FIG. 11. The operator may then extend the guide wire 112 from within the penetration member 108 towards the intima layer 1202 and may apply force to it to puncture the intima layer 1202. The guide wire 112 may puncture the intima layer 1202 and re-enter the true lumen 1208 of the vessel 1200.

Figure 18:
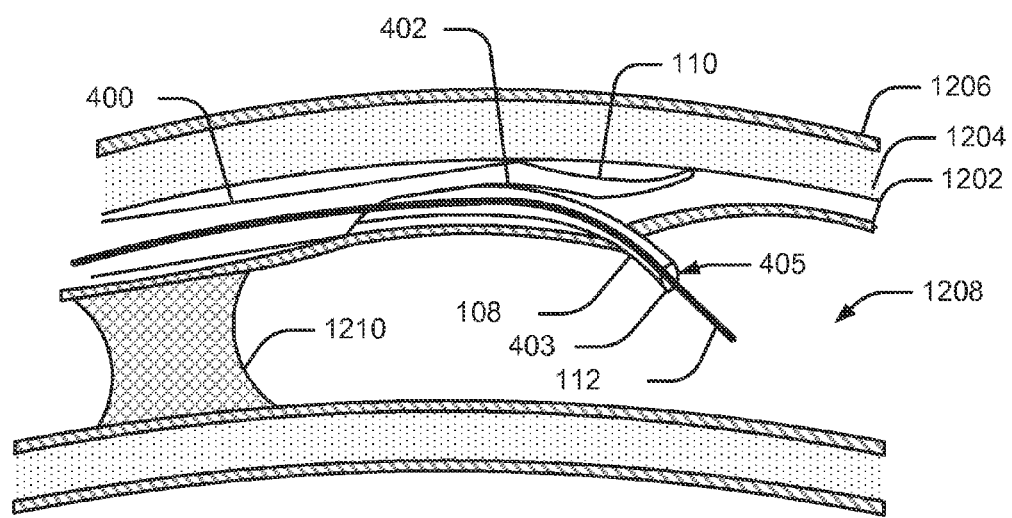
FIG. 18 exhibits the penetration member of the catheter apparatus of FIGS. 4A and 4B penetrating through the intima layer of the vessel wall.

Alternatively, as shown in FIG. 18, the deflection of the penetration member 108 with the sharp distal tip 403 may puncture the intima layer 1202 to create a re-entry path for the guide wire 112 by positioning the port 405 within the true lumen 1208 of the vessel 1200.

Once a re-entry path is created across the occlusion 1210, either through the occlusion 1210 or around the occlusion 1210 via a subintimal track, one or more additional medical devices may be advanced through the blood vessel 1200 to enlarge the pathway and/or pass distally of the occlusion 1210 to perform a further medical procedure.

Those skilled in the art will recognize that aspects of the present disclosure may be manifested in a variety of forms other than the specific embodiments described and contemplated herein. Accordingly, departure in form and detail may be made without departing from the scope and spirit of the present disclosure as described in the appended claims.

What is claimed is:

1. A subintimal recanalization catheter, comprising: an elongate shaft including a first tubular member and a penetration member slidably disposed in a lumen of the first tubular member, wherein the penetration member is configured to puncture an intima layer of a blood vessel: the penetration member including a distal tip, a first guide wire exit port at the distal tip, and a guide wire lumen extending through the penetration member, the distal tip positioned proximal of a distal nose of the first tubular member; and the distal nose of the first tubular member including a ramp and a guide wire lumen distal of the ramp and extending through the distal nose of the first tubular member; a guide wire extending through the guide wire lumen of the penetration member and through the guide wire lumen of the distal nose of the first tubular member; wherein longitudinal movement of the penetration member relative to the first tubular member causes the penetration member to contact the ramp to direct the distal tip of the penetration member away from the first tubular member while the guide wire is routed through the first tubular member proximal of the ramp and the guide wire lumen of the distal nose of the first tubular member distal of the ramp without passing through the first guide wire exit port.

2. The subintimal recanalization catheter of claim 1, wherein the penetration member includes a second guide wire exit port located proximal of the distal tip, wherein the guide wire is permitted to selectively exit the guide wire lumen of the penetration member and extend distally from one of the first guide wire exit port and the second guide wire exit port.

3. The subintimal recanalization catheter of claim 1, wherein the guide wire lumen extending through the distal nose extends from the ramp to a distal tip of the distal nose.

4. The subintimal recanalization catheter of claim 3, wherein the penetration member includes a second guide wire exit port proximal of the distal tip of the penetration member, and the guide wire extends from the second guide wire exit port to the guide wire lumen of the distal nose of the first tubular member.

5. The subintimal recanalization catheter of claim 1, wherein the guide wire lumen of the penetration member is co-axial with the lumen through the distal nose of the first tubular member.

6. The subintimal recanalization catheter of claim 1, wherein the penetration member includes a sharp distal tip.

7. A method of recanalizing a blood vessel having an occlusion therein, the method comprising:
   i) advancing a guide wire through a lumen of a blood vessel to a location proximal of a proximal end of an occlusion;
   ii) directing a distal end of the guide wire out of the lumen of the blood vessel and between a first tissue layer and a second tissue layer of a wall of the vessel to a location distal of a distal end of the occlusion;
   iii) advancing a recanalization catheter along the guide wire with the guide wire passing through a guide wire lumen of the recanalization catheter, the recanalization catheter including a first tubular member and a penetration member slidably disposed in a lumen of the first tubular member, the penetration member including a distal tip and a guide wire lumen extending through the penetration member, the distal tip positioned proximal of a distal nose of the first tubular member, the distal nose of the first tubular member including a ramp and the guide wire lumen located distal of the ramp and extending through the distal nose of the first tubular member;
   iv) positioning the distal nose of the first tubular member of the recanalization catheter between the first tissue layer and the second tissue layer at a location distal of the distal end of the occlusion;
   v) actuating the penetration member relative to the first tubular member to cause the penetration member to contact the ramp and direct the distal tip of the penetration member away from the first tubular member while the guide wire remains routed through the guide wire lumen of the distal nose of the first tubular member distal of the ramp; and
   vi) re-entering the lumen of the blood vessel distal of the distal end of the occlusion with the distal tip of the penetration member while the guide wire remains routed through the guide wire lumen of the distal nose of the first tubular member.

8. The method of claim 7, wherein the guide wire extends through the guide wire lumen of the penetration member while the recanalization catheter is advanced along the guide wire.

9. The method of claim 8, further comprising:
   vii) retracting the guide wire proximally of the distal tip of the penetration member.

10. The method of claim 8, wherein the guide wire lumen of the penetration member is co-axial with the guide wire lumen through the distal nose of the first tubular member.

11. The method of claim 8, wherein the penetration member includes a distal end region including a first guide wire exit port and a second guide wire exit port, wherein the first guide wire exit port is located at the distal tip of the penetration member and the second guide wire exit port is located proximal of the distal tip; and
   withdrawing the distal end of the guide wire proximally into the guide wire lumen of the penetration member through the second guide wire exit port; and
   then advancing the distal end of the guide wire distally out of the penetration member through the first guide wire exit port.

12. A subintimal recanalization catheter, comprising: a first tubular member including a lumen, a distal nose, a side opening proximal of the distal nose, and a ramp distal of the side opening, the distal nose of the first tubular member including a guide wire lumen distal of the ramp and extending through the distal nose of the first tubular member; a penetration member slidably disposed in the lumen of the first tubular member, the penetration member including a guide wire lumen and a sharp distal tip, the distal tip positionable proximal of the distal nose of the first tubular member in a delivery position, the penetration member further including a first guide wire exit port at the distal tip of the penetration member and a second guide wire exit port located proximal of the distal tip and distal of a proximal end of the penetration member, wherein both the first guide wire exit port and the second guide wire exit port are in communication with the guide wire lumen of the penetration member; a guide wire extending through the guide wire lumen of the penetration member, wherein the guide wire is permitted to selectively exit the guide wire lumen of the penetration member and extend distally from one of the first guide wire exit port and the second guide wire exit port; and wherein longitudinal movement of the penetration member relative to the first tubular member causes the penetration member to contact the ramp to direct the distal tip of the penetration member out of the side opening of the first tubular member; wherein the distal tip of the penetration member is deflectable away from the first tubular member while the guide wire is routed through the guide wire lumen of the distal nose of the first tubular member distal of the ramp without passing through the first guide wire exit port at the distal tip of the penetration member.

13. The subintimal recanalization catheter of claim 12, wherein the guide wire is configured to be withdrawn proximally into the guide wire lumen of the penetration member through the second guide wire exit port and then advanced distally out of the penetration member through the first guide wire exit port.

14. The subintimal recanalization catheter of claim 12, wherein the guide wire extends from the second guide wire exit port to the guide wire lumen of the distal nose of the first tubular member when the distal tip of the penetration member is in the delivery position.

* * * * *